(12) United States Patent
Braun et al.

(10) Patent No.: US 6,320,037 B2
(45) Date of Patent: Nov. 20, 2001

(54) IBD-ASSOCIATED MICROBIAL NUCLEIC ACID MOLECULES

(75) Inventors: Jonathan Braun, Tarzana; Christopher Sutton, Encinitas, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/820,576

(22) Filed: Mar. 28, 2001

Related U.S. Application Data

(62) Division of application No. 09/303,120, filed on Apr. 30, 1999.

(51) Int. Cl.$^7$ .................................................... C07H 21/04
(52) U.S. Cl. ...................... 536/23.7; 435/7.32; 424/190.1
(58) Field of Search ........................ 536/23.7; 435/7.32; 424/190.1

(56) References Cited

PUBLICATIONS

Nature, vol. 406, Aug. 31, 2000, pp. 959–964.*

\* cited by examiner

*Primary Examiner*—Laurie Scheiner
(74) *Attorney, Agent, or Firm*—Campbell & Flores LLP

(57) ABSTRACT

The present invention provides nucleic acid and amino acid sequence of the novel I-1 and I-2 polypeptides, which are associated with human inflammatory bowel disease (IBD). Methods of diagnosing and treating inflammatory bowel disease using the IBD-associated I-1 and I-2 antigens also are provided.

2 Claims, 8 Drawing Sheets

FIG. 1A

```
A GAT CTG GCC AGC GCC GTG GGC ATC CAG TCC GGC GAA ACC ATC TTT CAT CAC TTC AAG AGC AAG
▲ D  L   A   S   A   V   G   I   Q   S   G   E   T   I   F   H   H   F   K   S   K
GAT GAG ATA TTG CGT GCC GTG ATG GAG GAA ACC ATC CAT TAC AAC ACC GCG ATG ATG CGC
▲ D  E   I   L   R   A   V   M   E   E   T   I   H   Y   N   T   A   M   M   R
GCT TCA CTG GAG GCG AGC GCG GTG CGC GAA CGC GTG CTG GCG CTG ATC CGC ATG TGC GAG
▲ A  S   L   E   E   A   S   T   V   R   E   R   V   L   A   L   I   R   C   E
TTG CAG TCG ATC ATG GGC GGC AGT GGC CAC ATG GCG CTG GTC TAC GAA TGG CGC
▲ L  Q   S   I   M   G   G   S   G   H   M   A   L   V   Y   E   W   R
TCG CTG TCG GCC GAA GGC CAG GGC CTG CTG CGT GAC GTG TAT GAG CAG ATC T
▲ S  L   S   A   E   G   Q   G   L   L   R   D   V   Y   E   Q   I
```

FIG. 1B

```
AGATCTTGAGCTGTCATGAGTGCCTGGGGTACGCCTTTCATGCGTCCGGCGATCGAGAGTGGGTGT
▲ D  L   E   R   H   E   C   L   G   Y   A   F   S   S   R   P   A   D   R   E   W   V
                                             R   T   R   R   I   S   L   P   H
TTTTTCAGGGCACGGTTCCTACAAGTGACGTTCCAGCGTTGCTCATCAATGAAAGCCGGCA
F  F   Q   G   T   V   S   Y   K   V   R   V   A   S   R   L   L   I   N   E   S   R   A
KKK LAR NGV LYS HGA TQE DIF APC
TTGATGTCGGCGCATTGGATGGTTTTGGCATAGTGCTCGGCCAAGACTTCCTGCGAACGGCGTT
▲ L  M   S   A   A   L   D   G   F   I   V   L   G   P   Q   D   F   L   R   T   A   L
▲ Q  H   R   R   C   Q   I   T   K   A   Y   H   E   A   R   L   V   E   Q   S   R   R   Q
GGCGAGTGGCCGAGTTGGTGCGGGTTGTTGCCCGAGTTTGAGGCTTCCGAGTCGATGCATTGGTCT
▲ A  S   G   E   L   V   R   V   L   P   E   F   E   A   P   S   R   S   M   H   L   V
▲ R  T   A   L   Q   H   P   H   Q   R   L   K   L   S   R   T   P   R   H   M   Q   D
ACACCGCAAACCGCCAGCGTACCGCCAAGTTGCGCTGCTTTGTCGAGACTGTGCTGGGACGTTTTGGT
▲ Y  T   A   N   R   Q   R   T   A   K   L   R   C   F   V   E   T   V   L   G   R   F   G
▲ V  G   C   V   A   L   T   G   G   L   Q   A   A   K   D   L   S   H   Q   S   T   K   T
CCGGTATGAAGGAGCACCACCCTGCCGGTGCCGCGGANGCACCTAAAGATCT
▲ P  V
▲ R  Y   S   P   A   G   G   H   R   D   G   P   -   V
```

```
1-2            : ------------------------------MNK KDN FYS AIK V SNNGYNGA MDE : 1
Clostridium    : ---------MNK KDN FYS AIK V SNNGYNGA MDE                      : 28
Mycobacterium  : ---MDR VAGQ VNS RRGE LELAAAM AER GLRA T VR                   : 35
Aquifex        : MYI LLF MGEKRSD KEK LSS ALKL SKKGFKE T KD                    : 38
                                       a   f   g   t   d 1-2            : ASAV G QS GS  HHF KSKDE LRA MEET HYNTAM                       : 39
Clostridium    : IASNAGVA GTLY HF SKEE FKY IEEGVNL KNE                         : 66
Mycobacterium  : IADGAG L SGSLY HF ASKEEMV DELL RGFL DW FARY                   : 73
Aquifex        : IAKEVG TEGAIY RHF TSKEE I KS LLES TKE RHK                     : 76
                  6A    G6   G 65 HF  SKeE6      66e 1-2            : RAS EEAS VRE V LA  IRCE QS MGGSGEAMA LVY                      : 77
Clostridium    : DEAT DKEK ALEKLKAVCRVQ NL YKNRDF KV ASQ                       : 104
Mycobacterium  : RDI DSTANPLER QG FMASFEA EHHHAQVV YQDE                        : 111
Aquifex        : EVA QRGE DEE LES VDTL DYAFSNPES FRF NLY                       : 114
                        t     E 6   6                 i 1-2            : WRSLSA GQAHVLALR--DVYEQI------------- :  100
Clostridium    : WGKELR LELRDIMRN--YVVHIEEF KDA EAGSIK : 140
Mycobacterium  : QRLASQPRFSYIEDRNKQQRKMWVDV NQG EEGYFR : 149
Aquifex        : LLKEYG VKNLPGELI--LKFLNGLY KRK KT---Y : 147

1-2            : ------------------------------------- :  -
Clostridium    : GNS F AYAFLGTLCS SL YEVINAENDNINNTIENL : 178
Mycobacterium  : PDLD D VYRFIRDTTW S RWYRPGGPLTAQQVGQQY : 187
Aquifex        : PEIA A VT---GSVER F FKERNFLDYDEETIKKEL : 182
                                    V 1-2            : ----------- :  -
Clostridium    : MNY LNG GLQN- : 190
Mycobacterium  : LA V LGG TKEGV : 200
Aquifex        : KKV KSA LA--- : 192
                     l
```

FIG. 2

| Diagnosis | Tissue | | N | N(+) | %Pos |
|---|---|---|---|---|---|
| CD | Ileum | Involved | 46 | 25 | 54.3 |
| CD | Colon | Involved | 35 | 15 | 42.9 |
| CD | Ileum | Uninvolved | 14 | 6 | 42.9 |
| CD | Colon | Uninvolved | 26 | 5 | 19.2 |
| UC | Colon | Involved | 22 | 2 | 9.1 |
| UC | Colon | Uninvolved | 20 | 3 | 15.0 |
| Ca | Colon | Uninvolved | 15 | 2 | 13.3 |
| Ca | Ileum | Uninvolved | 7 | 3 | 42.9 |
| Divertic | Colon | Uninvolved | 7 | 0 | 0.0 |
| Append | Colon | Uninvolved | 5 | 0 | 0.0 |
| I-Col | Colon | Uninvolved | 15 | 0 | 0.0 |
| Total | | | 212 | 61 | |

FIG. 3

| Medium | Incubation | Organism |
|---|---|---|
| Trypticase soy agar | $O_2$ | Aerobes |
| McConkey | $O_2$ | *Enterobacteriae* |
| Sabouraud dextrose with Chloamphenical and gentamycin | $O_2$ | Yeast |
| Bile eculin agar | $O_2$ | *Enterococcus* |
| Chocolate | $CO_2$ | *Haemophilus* |
| CDC | An $O_2$ | Anaerobes |
| Brucella | An $O_2$ | Anaerobes |
| EYA+neomycin | An $O_2$ | *Clostridium* |
| EYA+heat treatment | An $O_2$ | *Clostridium* |
| CDC+heat treatments | An $O_2$ | *Clostridium* |
| CCFA+heat treatment | An $O_2$ | *C.difficile/Clostridium* |
| EYA+ethanol treatment | An $O_2$ | *Clostridium* |
| CDC+ethanol treatment | An $O_2$ | *Clostridium* |
| CCFA+ethanol treatment | An $O_2$ | *C.difficile/Clostridium* |
| BBE | An $O_2$ | BFG |
| LKV | An $O_2$ | Pigmenters |
| *Fusobacterium* selective medium | An $O_2$ | *Fusobacterium* |
| PEA | An $O_2$ | Gpc |
| CFA | An $O_2$ | *C.difficile* |
| LAMVAB | An $O_2$ | *Lactobacillus* |
| RB | An $O_2$ | *Bifidobacterium* |
| BBE+vancomycin | An $O_2$ | *Bilophila, Sutterella* |
| Modified BGSA for Camplyobacter | An $O_2$, 6%$O_2$(37C), 6%$O_2$(42C) | *Camplyobacter* |
| Campy CVA(CSL) | An $O_2$, 6%$O_2$(37C), 6%$O_2$(42C) | *Camplobacter* |
| Modified Skirrow | An $O_2$, 6%$O_2$(37C), 6%$O_2$(42C) | *Helicobacter pylori* |

FIG. 7

IBD-ASSOCIATED MICROBIAL NUCLEIC ACID MOLECULES

This application is a divisional of application Ser. No. 09/303,120, filed Apr. 30, 1999.

ACKNOWLEDGMENT

This work was supported by grant number DK46763 awarded by the National Institutes of Health. The United States government has certain rights in this invention.

BACKGROUND OF THE INVENTION

Filed of the Invention

The invention relates generally to the fields of immunology, microbiology and inflammatory bowel disease and more specifically to the diagnosis and treatment of inflammatory bowel disease using microbial antigens.

Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe, and anemia and weight loss are additional common signs of IBD. Ten percent to fifteen percent of all patients with IBD will require surgery over a ten year period. In addition, patients with IBD are at increased risk for the development of intestinal cancer. Reports of an increased occurrence of psychological problems, including anxiety and depression, are perhaps not surprising symptoms of what is often a debilitating disease that strikes people in the prime of life.

Unfortunately, the available therapies for inflammatory bowel disease are few, and both diagnosis and treatment have been hampered by a lack of knowledge regarding the etiology of the disease. What is clear, however, is that a combination of genetic factors, exogenous triggers and endogenous microflora can contribute to the immune-mediated damage to the intestinal mucosa seen in inflammatory bowel disease. In Crohn's disease, bacteria have been implicated in initiation and progression of the disease: the intestinal inflammation in Crohn's disease is notable for its frequent responsiveness to antibiotics and susceptibility to bacterial fecal flow. Common intestinal colonists and novel pathogens have been implicated in Crohn's by direct detection or by disease associated anti-microbial immune responses. Furthermore, in many genetically susceptible animal models of chronic colitis, lumenal micro-organisms are a necessary cofactor for disease; animals housed in a germ-free environment do not develop colitis. However, despite much direct and indirect evidence for a role for enteric microorganisms in Crohn's disease, the pathogenic organisms and antigens contributing to the immune dysregulation seen in this disease have not been identified.

Current diagnostic assays for Crohn's disease are unable to detect all patients with the disease. Thus, identification of novel microbial antigens associated with Crohn's disease would provide reagents that can increase the sensitivity of current diagnostic assays. In addition, such microbial antigens can bear a disease related T-cell epitope and, as original or contributing inducers of the disease-related immune response, can be effective tolerogenic antigens for treating inflammatory bowel disease. Identification of IBD-associated microbial antigens also would facilitate isolation of the involved microbial species, paving the way for the discovery of new antibiotics or drugs for treating inflammatory bowel disease, such drugs ameliorating disease by eliminating the microbial inducers of disease.

Thus, there is a need for identification and isolation of microbial IBD-associated antigens for diagnosing and treating the many individuals suffering from inflammatory bowel disease. The present invention satisfies this need by providing the IBD-associated I-1 and I-2 microbial antigens. Related advantages are provided as well.

SUMMARY OF THE INVENTION

The present invention provides an isolated inflammatory bowel disease-associated I-2 polypeptide having substantially the same amino acid sequence as SEQ ID NO: 2. The invention also provides an isolated immunoreactive fragment of an I-2 polypeptide having substantially the same amino acid sequence as a portion of SEQ ID NO: 2. An isolated immunoreactive fragment of an I-2 polypeptide can have, for example, at least ten contiguous amino acids of SEQ ID NO: 2.

Also provided by the present invention is substantially purified antibody material that selectively binds an I-2 polypeptide having SEQ ID NO: 2. Such a substantially purified antibody material can be, for example, substantially purified polyclonal or monoclonal antibody material.

The invention further provides an isolated nucleic acid molecule having a nucleic acid sequence encoding substantially the same amino acid sequence as SEQ ID NO: 2. An isolated nucleic acid molecule of the invention can have, for example, the nucleic acid sequence SEQ ID NO: 1.

Also provided by the invention is a method of diagnosing inflammatory bowel disease (IBD) in a subject. The method includes the steps of obtaining a sample from the subject; contacting the sample with an I-2 polypeptide, or immunoreactive fragment thereof, under conditions suitable to form a complex of the I-2 polypeptide, or the immunoreactive fragment thereof, and antibody to the I-2 polypeptide; and detecting the presence or absence of the complex, where the presence of the complex indicates that the subject has IBD. A method of the invention for diagnosing inflammatory bowel disease can be useful, for example, for diagnosing Crohn's disease. In a method of the invention for diagnosing inflammatory bowel disease, the presence or absence of the complex can be detected, for example, with a detectable secondary antibody that has specificity for a class determining portion of the antibody to the I-2 polypeptide.

Further provided by the invention is a method of inducing tolerance in a patient with inflammatory bowel disease by administering an effective dose of an I-2 polypeptide, or tolerogenic fragment thereof, to the patient with IBD. The methods of the invention can be particularly useful for treating a patient having Crohn's disease. In a method of the invention for inducing tolerance, the I-2 polypeptide to be administered can have, for example, the amino acid sequence of SEQ ID NO: 2.

The invention also provides a composition including an I-2 polypeptide having substantially the same amino acid sequence as SEQ ID NO: 2, or tolerogenic fragment thereof, combined with a tolerogizing molecule. In a composition of the invention, the I-2 polypeptide can have, for example, the amino acid sequence SEQ ID NO: 2. A tolerogenic fragment useful in a composition of the invention can have, for example, at least ten contiguous amino acids of SEQ ID NO: 2.

The present invention also provides a method of identifying an agent useful in treating inflammatory bowel disease. The method includes the steps of obtaining a specimen of an enteric microbe from a patient with inflammatory bowel disease; isolating from the specimen a microbial species that includes a nucleic acid molecule encoding an I-2 polypeptide; contacting the microbial species with an agent; and assaying for reduced growth or viability of the microbial species as compared to the growth or viability in the absence of the agent, where the reduced growth or viability of the microbial species indicates that the agent is an agent useful in treating inflammatory bowel disease. A method of the invention can be useful, for example, for identifying an agent for treating Crohn's disease. The methods of the invention can be particularly useful for screening agents which are antibiotics.

The invention additionally provides a method of identifying an agent useful in treating inflammatory bowel disease using a novel animal model. The method includes the steps of administering an I-2 polypeptide to a non-human animal, whereby one or more symptoms of IBD are exhibited; administering an agent to the non-human animal; and assaying the level of the one or more symptoms characteristic of IBD, where a reduction in the level of the one or more symptoms as compared to a control level indicates that the agent is an agent useful in treating IBD. The methods of the invention can be applied, for example, to identification of agents useful in treating Crohn's disease. The I-2 polypeptide administered can have, for example, the amino acid sequence SEQ ID NO: 2. A non-human animal particularly useful in the methods of the invention can be, for example, a mouse deficient in Gαi2, TCRα or IL-10.

BRIEF DESCRIPTION OF THE DRAWINGS

FIGS. 1A and 1B show the I-1 and I-2 nucleic acid sequences and encoded polypeptides. A. Shown are the I-2 nucleic acid sequence (SEQ ID NO: 1) and predicted amino acid sequence (SEQ ID NO: 2). B. Shown are the I-1 nucleic acid sequence (SEQ ID NO: 3) and I-1 open reading frame 1 (top; SEQ ID NO: 4) and open reading frame 2 (bottom; SEQ ID NO: 5).

FIG. 2 shows an alignment of the I-2 amino acid sequence SEQ ID NO: 2 with homologous sequences. Sequences were identified by tBLASTx search against the non-redundant database. Alignments were generated by CLUSTALW, with modifications by Genedoc. "Clostridium" is the predicted protein 4 from *Clostridium pasteurianum* (SEQ ID NO: 6; accession number 481591); "Mycobacterium" is the predicted protein Rv3557c from *Mycobacterium tuberculosis* (SEQ ID NO: 7; accession number 1877288); and "Aquifex" is a transcriptional regulator from *Aquifex aeolicus* (SEQ ID NO: 8; accession number 2984362). Residues identical or conservatively substituted among four polypeptides are shown in black; residues identical or conservatively substituted among three polypeptides are shown in dark gray; and residues identical or conservatively substituted between two polypeptides are shown in light gray. Consensus residues are shown beneath the alignment, with one-letter codes indicating conserved amino acids; "6" indicating a conserved non-polar (hydrophobic) residue such as leucine, isoleucine, alanine, valine or methionine; and "5" indicating the conserved aromatic residue phenylalanine or tyrosine.

FIG. 3 shows the results of PCR analysis with I-2 (SEQ ID NO: 1) specific primers using paraffin embedded colonic samples from CD patients, UC patients and control individuals. "N" designates the number of samples assayed, and "N+" designates the number of positive samples. "Ca" designates cancer resection samples; "Divertic" designates diverticulitis samples; "append" designates appendicitis samples; and "I-col" designates ischemic colitis.

A. Sera from Crohn's disease patients and normal individuals was assayed by ELISA at the indicated dilutions for IgG reactivity to the GST-I-2 fusion polypeptide (SEQ ID NO: 2). The absorbance values were calculated by subtracting absorbance to GST alone.

B. Sera from Crohn's disease, ulcerative colitis and normal individuals was assayed by ELISA for IgA reactivity to the GST-I-2 fusion polypeptide (SEQ ID NO: 2). The absorbance values were calculated by subtracting absorbance to GST alone. The cut-off (dotted line) was set as two standard deviations above the mean value for the normal population.

Figure 5:
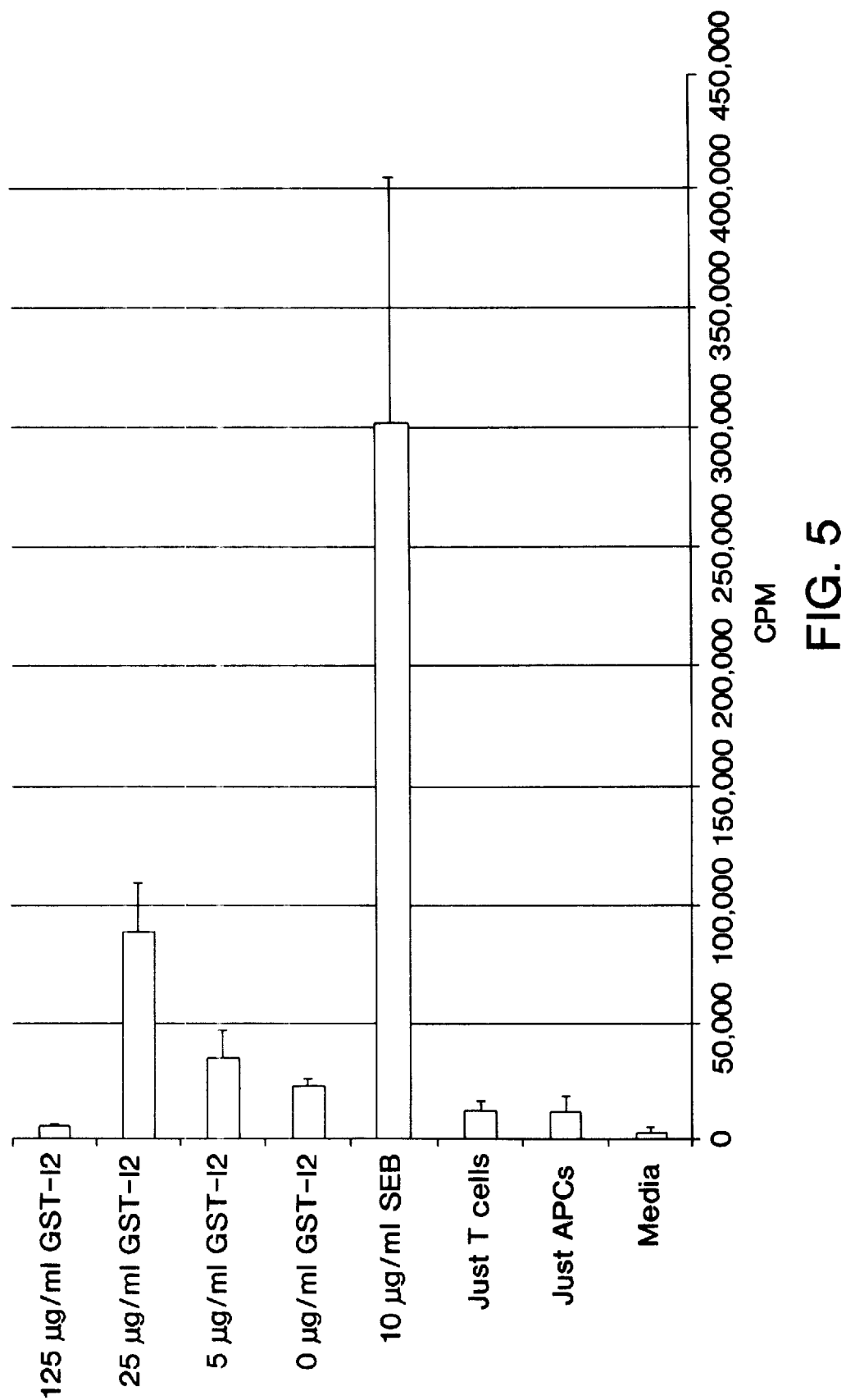

FIG. 5 shows T cell proliferation assays using CD4+ T cells derived from normal C57BL/6J mice. T cells were stimulated with the indicated concentration of GST-I-2 fusion protein, shown on the Y axis. The X axis represents counts of incorporated [$^3$H]-thymidine. SEB represents T cells stimulated with the positive control *Staphylococcus aureus* enterotoxin B.

Figure 6:
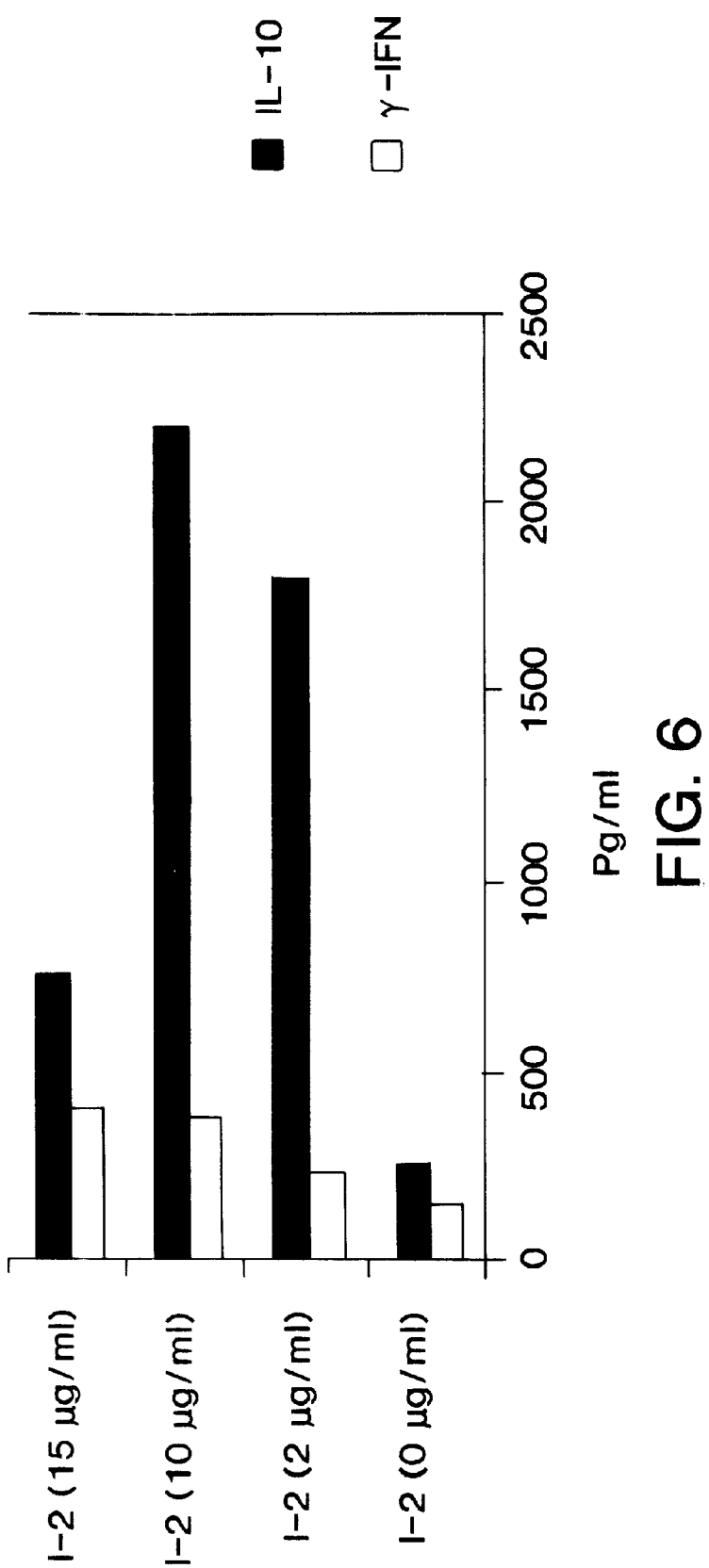

FIG. 6 shows T cell cytokine expression in response to challenge with the GST-I-2 fusion protein.

FIG. 7 shows a variety of conditions for culturing microbial organisms isolated from IBD patients.

DETAILED DESCRIPTION OF THE INVENTION

The pathogenesis of inflammatory bowel disease, although poorly understood, ultimately involves immune-mediated tissue damage. Similar to autoimmune disorders such as diabetes mellitus and multiple sclerosis, inflammatory bowel disease is associated with various immunologic abnormalities and can represent a process of immune dysfunction. However, unlike the other disorders, inflammatory bowel disease occurs in a mucosal site interfacing with the intestinal lumen, and, therefore, a primary immune target in inflammatory bowel disease can be extrinsic agent such as a chronic microbial colonist. In this case, the mucosal injury characteristic of inflammatory bowel disease is a consequence of inflammatory bystander damage to resident parenchymal cells.

The present invention is directed to the exciting discovery that several microbial DNA sequences are found preferentially in involved Crohn's disease (CD) mucosa as compared to uninvolved mucosa. As disclosed herein, representational difference analysis (RDA), a PCR driven subtractive cloning approach for identifying DNA sequences found preferentially in an infected area, was used to isolate DNA sequences from a Crohn's disease patient that were differentially present in mononuclear cells from the lamina propria in an area with ulcerations as compared to an area macroscopically free of disease (see Example I). As disclosed herein, two IBD-associated sequences were of microbial origin. The nucleic acid and amino acid sequences, designated I-1 (SEQ ID NOS: 3 to 5) and I-2 (SEQ ID NOS: 1 and 2) are shown in FIG. 1. As further disclosed herein, PCR analysis of colonic samples from CD, UC and non-IBD patients revealed that the I-2 sequence (SEQ ID NO: 1) was more often found in involved CD tissue than in UC or non-IBD samples (Example I and FIG. 3). Thus, novel microbial sequences have been identified that are associated with inflammatory bowel disease, in particular, with inflamed CD lesions. Isolation of microbial sequences associated with IBD implicates microbes in the pathogenesis of IBD and provides valuable reagents for diagnosing or ameliorating inflammatory bowel disease.

Thus, the present invention provides an isolated inflammatory bowel disease associated I-2 polypeptide having substantially the same amino acid sequence as SEQ ID NO: 2. The invention also provides an isolated immunoreactive fragment of an I-2 polypeptide having substantially the same amino acid sequence as a portion of SEQ ID NO: 2. An isolated immunoreactive fragment of an I-2 polypeptide can have, for example, at least ten contiguous amino acids of SEQ ID NO: 2.

The term "isolated," as used herein in reference to a polypeptide means a polypeptide that is in a form that is relatively free from contaminating lipids, polypeptides, nucleic acids or other cellular material normally associated with the polypeptide in a cell.

As used herein, the term "I-2 polypeptide" means a polypeptide having substantially the same amino acid sequence as the microbial I-2 polypeptide (SEQ ID NO: 2) shown in FIG. 1A. The microbial I-2 polypeptide (SEQ ID NO: 2) is a polypeptide of 100 amino acids sharing some similarity to bacterial transcriptional regulators, with the greatest similarity in the amino-terminal 30 amino acids. As illustrated in FIG. 2, the I-2 polypeptide shares weak homology with the predicted protein 4 from *C. pasteurianum* (SEQ ID NO: 6); Rv3557c from *Mycobacterium tuberculosis* (SEQ ID NO: 7); and a transcriptional regulator from *Aquifex aeolicus* (SEQ ID NO: 8). As disclosed in Example I, the I-2 encoding nucleic acid (SEQ ID NO: 1) is differentially present in involved Crohn's disease tissue, as compared to mucosa macroscopically free of disease.

An I-2 polypeptide having substantially the same amino acid sequence as SEQ ID NO: 2 can be the naturally occurring I-2 polypeptide (SEQ ID NO: 2) or a related polypeptide having substantial amino acid sequence similarity to this sequence. Such related polypeptides exhibit greater sequence similarity to the I-2 polypeptide SEQ ID NO: 2 than to the *C. pasteurianum* sequence SEQ ID NO: 6 and include isotype variants or homologs of the amino acid sequence shown in FIG. 1A. As used herein, the term I-2 polypeptide generally describes polypeptides generally having an amino acid sequence with greater than about 50% identity, preferably greater than about 60% identity, more preferably greater than about 70% identity, and can be a polypeptide having greater than about 80%, 90%, 95%, 97%, or 99% amino acid sequence identity with SEQ ID NO: 2, said amino acid identity determined with CLUSTALW using the BLOSUM 62 matrix with default parameters. The *C. pasteurianum* protein 4 (SEQ ID NO: 6) has about 21% amino acid identity with the I-2 polypeptide SEQ ID NO: 2 and, therefore, is not an I-2 polypeptide as defined herein.

The I-1 nucleic acid sequence (SEQ ID NO: 3) contains two open reading frames (ORFs) on opposite strands. The top strand I-1 ORF shown in FIG. 1B encodes a predicted polypeptide of 115 amino acids (SEQ ID NO: 4) with homology to the prokaryotic transcription factor ptxR. The bottom strand ORF encodes a predicted polypeptide of 114 amino acids (SEQ ID NO: 5). The I-1 encoding nucleic acid (SEQ ID NO: 3) also was isolated by RDA analysis as a sequence preferentially found in involved CD mucosa (see Example I).

An I-1 polypeptide can have substantially the same amino acid sequence as SEQ ID NO: 4 or SEQ ID NO: 5. Such an I-1 polypeptide can be a naturally occurring I-1 polypeptide (SEQ ID NOS: 4 or 5) or a related polypeptide, for example, an isotype variant or homologous sequence from a different bacterial species having substantial amino acid sequence similarity to one of these sequences. As used herein, the term I-1 polypeptide generally describes polypeptides generally having an amino acid sequence with greater than about 50% identity, preferably greater than about 60% identity, more preferably greater than about 70% identity, and can be a polypeptide having greater than about 80%, 90%, 95%, 97%, or 99% amino acid sequence identity with SEQ ID NOS: 4 or 5, said amino acid identity determined with CLUSTALW using the BLOSUM 62 matrix with default parameters.

As used herein, the term "substantially the same amino acid sequence," when used in reference to an I-1 or I-2 polypeptide, is intended to mean a sequence as shown in FIG. 1A or FIG. 1B, or a similar, non-identical sequence that is considered by those skilled in the art to be a functionally equivalent amino acid sequence. For example, an amino acid sequence that has substantially the same amino acid sequence as an I-1 polypeptide (SEQ ID NOS: 4 or 5) or I-2 polypeptide (SEQ ID NO: 2) can have one or more modifications such as amino acid additions, deletions or substitutions relative to the amino acid sequence of SEQ ID NO: 4 or 5, or SEQ ID NO: 2, respectively, provided that the modified polypeptide retains substantially at least one biological activity of I-1 or I-2 such as immunoreactivity or tolerogenic activity, described further below. Comparison for substantial similarity between amino acid sequences is usually performed with sequences between about 6 and 100 residues, preferably between about 10 and 100 residues and more preferably between about 25 and 35 residues.

Thus, it is understood that limited modifications can be made to an I-1 or I-2 polypeptide, or to an immunoreactive or tolerogenic fragment thereof, as described further below, without destroying its biological function. A modification of an I-1 or I-2 polypeptide that does not destroy immunoreactivity or a modification of an I-1 or I-2 polypeptide that does not destroy tolerogenic activity is encompassed within the meaning of the term I-1 polypeptide, or I-2 polypeptide, as used herein. A modification can be, for example, an addition, deletion, or substitution of one or more amino acid residues; substitution of a compound that mimics amino acid structure or function; or addition of chemical moieties such as amino or acetyl groups. The activity of a modified I-1 or I-2 polypeptide or fragment thereof can be assayed, for example, using one of the assays for immunoreactivity or tolerogenic activity disclosed herein (see below).

A particularly useful modification of a polypeptide of the invention, or fragment thereof, is a modification that confers, for example, increased stability. Incorporation of one or more D-amino acids is a modification useful in increasing stability of a polypeptide or polypeptide fragment. Similarly, deletion or substitution of lysine can increase stability by protecting against degradation. For example, such a substitution can increase stability and, thus, bioavailability of one of the polypeptide antigens disclosed herein.

The I-2 polypeptide, and fragments thereof, can be useful to prepare substantially purified antibody material that selectively binds an I-2 polypeptide (SEQ ID NO: 2). The antibody material can be, for example, substantially purified polyclonal antiserum or monoclonal antibody material. The antibody material of the invention be useful, for example, in determining the presence and location of I-2 polypeptide within the mucosa of afflicted patients and in diagnosing inflammatory bowel disease. The substantially purified antibody material of the invention can be useful, for example, in an ELISA or immunohistopathological assay for diagnosing Crohn's disease.

As used herein, the term "antibody material" is used in its broadest sense to include polyclonal and monoclonal antibodies, as well as polypeptide fragments of antibodies that retain a selective binding activity for an I-2 polypeptide of at least about $1 \times 10^5$ M$^{-1}$. One skilled in the art would know that anti-I-2 antibody fragments such as Fab, F(ab')$_2$ and Fv fragments can retain selective binding activity for an I-2 polypeptide and, thus, are included within the definition of an antibody. In addition, the term antibody material as used herein encompasses non-naturally occurring antibodies and fragments containing, at a minimum, one $V_H$ and one $V_L$ domain, such as chimeric antibodies, humanized antibodies, single chain Fv fragments (scfv) that selectively bind an I-2 polypeptide. Such non-naturally occurring antibodies can be constructed using solid phase peptide synthesis, produced recombinantly or obtained, for example, by screening combinatorial libraries consisting of variable heavy chains and variable light chains as described by Borrebaeck (Ed.), *Antibody Engineerinq* (Second edition) New York: Oxford University Press (1995), which is incorporated herein by reference.

Antibody material "selective for" an I-2 polypeptide, or that "selectively binds" an I-2 polypeptide, binds with substantially higher affinity to that polypeptide than to an unrelated polypeptide. The substantially purified antibody material of the invention also can be specific for an I-2 polypeptide, whereby its binding affinity is significantly higher for an I-2 polypeptide than for related polypeptides such as SEQ ID NOS: 6 to 8.

Anti-I-2 antibody material can be prepared, for example, using an I-2 fusion protein or a synthetic peptide encoding a portion of the I-2 polypeptide (SEQ ID NO: 2) as an immunogen. One skilled in the art would know that purified I-2 polypeptide, which can be produced recombinantly, or fragments of I-2, including peptide portions of I-2 such as synthetic peptides, can be used as an immunogen. Non-immunogenic fragments or synthetic peptides of I-2 can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art as described, for example, by Harlow and Lane, *Antibodies: A Laboratory Manual* (Cold Spring Harbor Laboratory Press, 1988), which is incorporated herein by reference.

The term "substantially purified," as used herein in reference to antibody material, means that the antibody material is substantially devoid of polypeptides, nucleic acids and other cellular material which with an antibody is normally associated in a cell. The claimed antibody material that selectively binds an I-2 polypeptide (SEQ ID NO: 2) further is substantially devoid of antibody material of unrelated specificities, i.e. that does not selectively bind an I-2 polypeptide. The antibody material of the invention can be prepared in substantially purified form, for example, by I-2 affinity purification of polyclonal anti-I-2 antisera, by screening phage displayed antibodies against the I-2 polypeptide (SEQ ID NO: 2), or as monoclonal antibodies prepared from hybridomas.

The invention further provides an isolated nucleic acid molecule having a nucleic acid sequence encoding substantially the same amino acid sequence as SEQ ID NO: 2. An isolated nucleic acid molecule of the invention can have, for example, the nucleic acid sequence SEQ ID NO: 1. These nucleic acid molecules are useful, for example, in producing recombinant polypeptides and as probes for detecting I-2 mRNA expression. Nucleotide portions of SEQ ID NO: 1 also are useful, for example, as primers for PCR analysis (see Example I).

Isolated nucleic acid molecules of the invention include, for example, nucleic acid molecules encoding I-2 polypeptide homologs, nucleic acid molecules that are related, but different and encode the polypeptide of SEQ ID NO: 2 due to the degeneracy of the genetic code, and nucleic acid molecules that are related, but different and encode an I-2 polypeptide different from SEQ ID NO: 2 that exhibits immunoreactivity or tolerogenic activity.

The methods of the invention relate to the diagnosis and treatment of inflammatory bowel disease, which is a designation that encompasses the broad categories of Crohn's disease and ulcerative colitis. Crohn's disease (regional enteritis) is a disease of chronic inflammation that can involve any part of the gastrointestinal tract. Commonly the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of CD are abdominal pain, diarrhea and recurrent fever. CD is commonly associated with intestinal obstruction or fistula, which is an abnormal passage between diseased loops of bowel, for example. Crohn's disease also includes complications such as inflammation of the eye, joints and skin; liver disease; kidney stones or amyloidosis. In addition, CD is associated with an increased risk of intestinal cancer.

Several features are characteristic of the pathology of Crohn's disease. The inflammation associated with CD, known as transmural inflammation, involves all layers of the bowel wall. Thickening and edema, for example, typically also appear throughout the bowel wall, with fibrosis also present in long-standing disease. The inflammation characteristic of CD also is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of Crohn's disease is the presence of discrete aggregations of inflammatory cells, known as granulomas, which are generally found in the submucosa. Some Crohn's disease cases display the typical discrete granulomas, while others show a diffuse granulomatous reaction or nonspecific transmural inflammation. As a result, the presence of discrete granulomas is indicative of CD, although the absence of granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J. B. Lippincott Company (1994), which is incorporated herein by reference).

Ulcerative colitis (UC) is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerated intestinal crypts are filled with neutrophils, also are typical of ulcerative colitis (Rubin and Farber, supra, 1994).

In comparison with Crohn's disease, which is a patchy disease with frequent sparing of the rectum, ulcerative colitis is characterized by a continuous inflammation of the colon that usually is more severe distally than proximally. The inflammation in ulcerative colitis is superficial in that it is usually limited to the mucosal layer and is characterized by an acute inflammatory infiltrate with neutrophils and crypt abscesses. In contrast, Crohn's disease affects the entire thickness of the bowel wall with granulomas often, although not always, present. Disease that terminates at the ileocecal valve, or in the colon distal to it, is indicative of ulcerative colitis, while involvement of the terminal ileum, a cobblestone-like appearance, discrete ulcers or fistulas suggest Crohn's disease. Characteristics that serve to distinguish Crohn's disease from ulcerative colitis are summarized in Table 1 (Rubin and Farber, supra, 1994).

TABLE 1

Characteristic Features of Crohn's disease and ulcerative colitis

| Feature | Crohn's Disease | Ulcerative Colitis |
| --- | --- | --- |
| Macroscopic | | |
| Thickened bowel wall | Typical | Uncommon |
| Luminal narrowing | Typical | Uncommon |
| "Skip" lesions | Common | Absent |
| Right colon predominance | Typical | Absent |
| Fissures and fistulas | Common | Absent |
| Circumscribed ulcers | Common | Absent |
| Confluent linear ulcers | Common | Absent |
| Pseudopolyps | Absent | Common |
| Microscopic | | |
| Transmural inflammation | Typical | Uncommon |
| Submucosal fibrosis | Typical | Absent |
| Fissures | Typical | Rare |
| Granulomas | Common | Absent |
| Crypt abscesses | Uncommon | Typical |

Certain immune-mediated disorders, including systemic lupus erythematosis, primary biliary cirrhosis and autoimmune hepatitis, are closely associated with distinctive patterns of autoantibody production. Disease-specific marker antibodies also have been observed in IBD. In the case of ulcerative colitis, anti-neutrophil cytoplasmic antibodies that produce a perinuclear staining pattern (pANCA), for example, upon indirect immunofluorescence microscopy of alcohol-fixed neutrophils, are elevated in 68–80% of UC patients and less frequently in other disorders of the colon. In Crohn's disease, serum reactivity to the cell wall mannan polysaccharide of *Saccharonyces uvarum* (brewer's yeast) is a serologic marker for a majority of individuals with Crohn's disease (Sendid et al., *Clin. Diag. Lab. Immunol.*, 3:219–226 (1996), which is incorporated herein by reference).

Figure 4A:
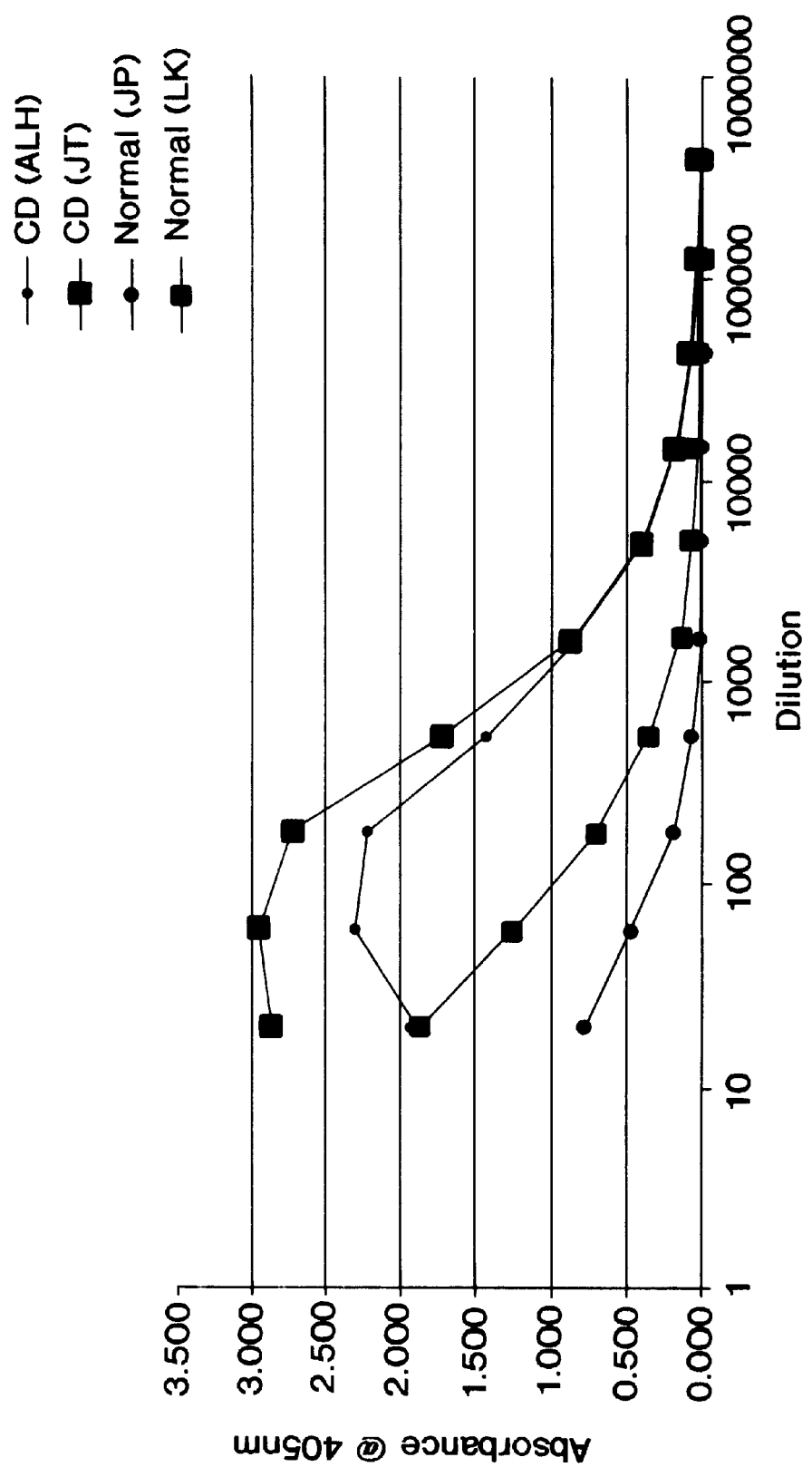
FIG. 4A and 4B show IgG and IgA reactivities to the I-2 polypeptide (SEQ ID NO: 2) in various populations.
Figure 4B:
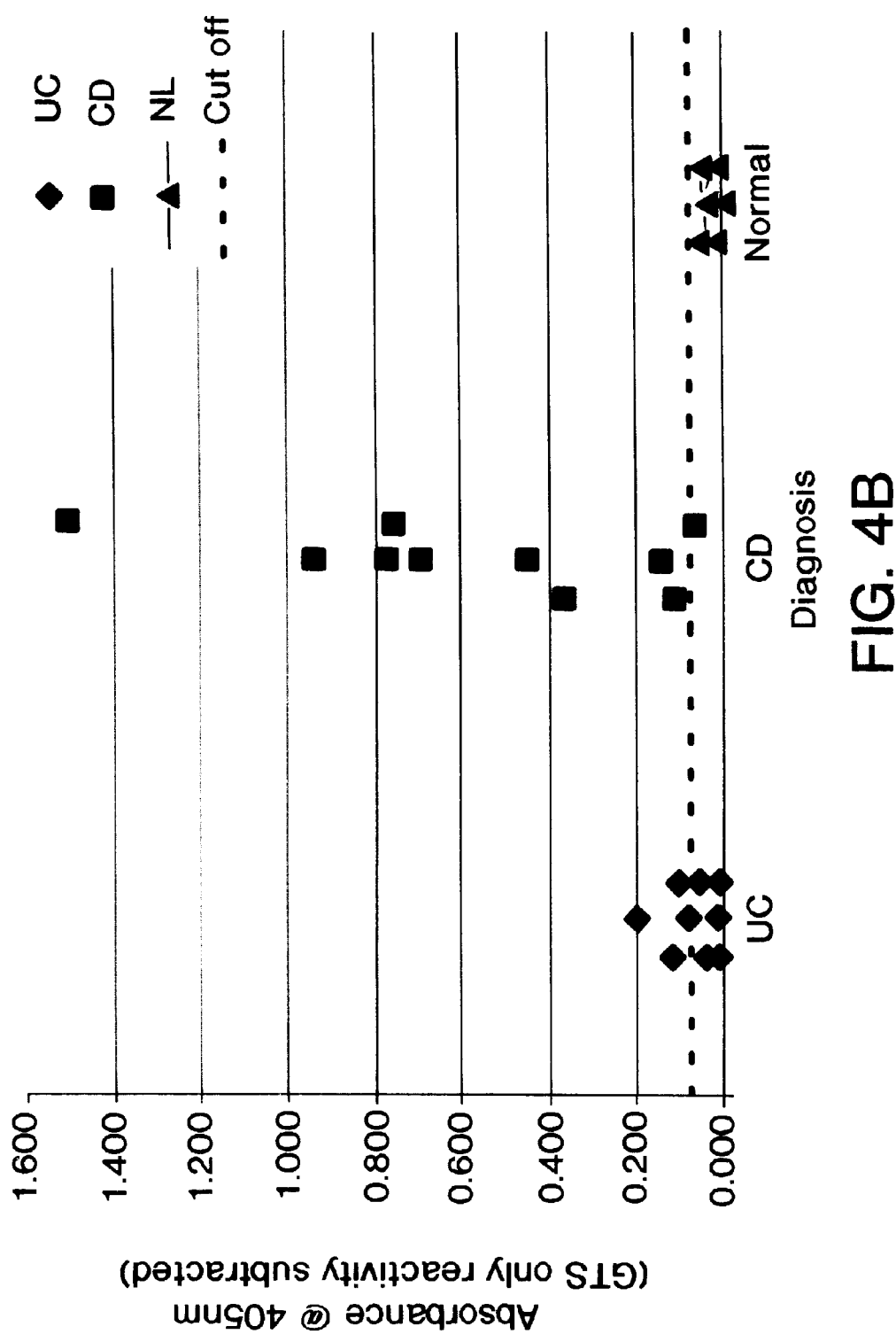

As disclosed herein, ELISA analysis showed increased IgG serum reactivity to a GST-I-2 fusion polypeptide (SEQ ID NO: 2) in patients with Crohn's disease as compared to normal individuals (see FIG. 4A). As shown in FIG. 4B, 9 of 10 Crohn's disease patients had IgA serum reactivity to the GST-I-2 fusion polypeptide greater than two standard deviations above the mean value for a normal population. In contrast, no normal serum samples contained anti-I-2 IgA reactivity above this cutoff. The anti-I-2 serum IgA reactivity also was significantly higher on average in samples from Crohn's disease patients as compared to ulcerative colitis patients. These results indicate that reactivity to the I-2 polypeptide (SEQ ID NO: 2) can be used to differentiate Crohn's disease from normal individuals and those with UC.

Based on the above findings, the present invention provides methods of diagnosing inflammatory bowel disease (IBD) in a subject. The methods include the steps of obtaining a sample from the subject; contacting the sample with an I-2 polypeptide, or immunoreactive fragment thereof, under conditions suitable to form a complex of the I-2 polypeptide, or the immunoreactive fragment thereof, and antibody to the I-2 polypeptide; and detecting the presence or absence of the complex, where the presence of the complex indicates that the subject has IBD. A method of the invention for diagnosing inflammatory bowel disease can be useful, for example, for diagnosing Crohn's disease. The presence or absence of the complex can be detected, for example, with a detectable secondary antibody that has specificity for a class determining portion of the antibody to the I-2 polypeptide.

As used herein, the term "subject" means any animal capable of having inflammatory bowel disease, including a human, non-human primate, rabbit, rat or mouse, especially a human. A subject generally has one or more symptoms of ulcerative colitis or Crohn's disease.

A sample useful in the methods of the invention can be obtained from any biological fluid having antibodies such as, for example, whole blood, plasma, saliva, or other bodily fluid or tissue, preferably serum. A sample to be assayed according to the methods of the invention can be obtained from any such subject.

As used herein, the term "complex" is synonymous with "immune complex" and means an aggregate of two or more molecules that results from specific binding between an antigen, such as a protein or peptide, and an antibody. In the methods of the invention, a complex is formed by specific binding of an I-2 polypeptide to an antibody.

In the methods of the invention, a complex can be detected with a detectable secondary antibody that has specificity for a class determining portion of the antibody to the I-2 polypeptide. Such a secondary antibody can be, for example, an anti-IgA secondary antibody, an anti-IgG secondary antibody, or a combination of anti-IgA and anti-IgG secondary antibodies.

As used herein, the term "secondary antibody" means an antibody or combination of antibodies, which binds an antibody that specifically binds an I-2 polypeptide having substantially the amino acid sequence SEQ ID NO: 2. One skilled in the art understands that, preferably, a secondary antibody does not compete with the I-2 antigen for binding to the primary antibody. A secondary antibody can bind any epitope of the antibody that specifically binds the I-2 polypeptide. A particularly useful secondary antibody is an anti-IgA or anti-IgG antibody having specificity for the class determining portion of the primary antibody. A useful secondary antibody is specific for the species from which the sample was obtained. For example, if human serum is the sample to be assayed, mouse anti-human IgA or IgG can be a useful secondary antibody. A combination of different antibodies, which can be useful in the methods of the invention, also is encompassed within the meaning of the term secondary antibody, provided that at least one antibody of the combination reacts with an antibody that specifically binds an I-2 polypeptide.

As used herein, the term "class determining portion," when used in reference to a secondary antibody, means the heavy chain constant-region sequence of an antibody that determines the isotype, such as IgA, IgD, IgE, IgG or IgM. Thus, a secondary antibody that has specificity for the class determining portion of an IgA molecule, for example, binds IgA in preference to other antibody isotypes.

A secondary antibody useful in the invention can be obtained commercially or by techniques well known in the art. Such an antibody can be a polyclonal or, preferably, monoclonal antibody. For example, IgG reactive polyclonal antibodies can be prepared using IgG or Fc fragments of IgG as an immunogen to stimulate the production of antibodies in the antisera of an animal such as a rabbit, goat, sheep or rodent, as described in Harlow and Lane, *Antibodies: A Laboratory Manual* New York: Cold Spring Harbor Laboratory (1988), which is incorporated herein by reference. Monoclonal secondary antibodies, which are a population of antibody molecules that contain only one species of idiotype capable of binding a particular antigen epitope also can be produced by routine methods (see, for example, Harlow and Lane, supra, 1988) or obtained commercially.

The term "detectable secondary antibody" means a secondary antibody, as defined above, that can be detected or measured by analytical methods. Thus, the term secondary antibody includes an antibody labeled directly or indirectly with a detectable marker that can be detected or measured and used in a convenient assay such as an enzyme-linked immunosorbent assay, radioimmunoassay, radial immunodiffusion assay or Western blotting assay. A secondary antibody can be labeled, for example, with an enzyme, radioisotope, fluorochrome or chemiluminescent marker. In addition, a secondary antibody can be rendered detectable using a biotin-avidin linkage such that a detectable marker is associated with the secondary antibody. Labeling of the secondary antibody, however, should not impair binding of the secondary antibody to the I-2 polypeptide. If desired, a multiple antibody system can be used as the secondary antibody as discussed above. In such a system, at least one of the antibodies is capable of binding the primary anti-I-2 antibody and at least one of the antibodies can be readily detected or measured by analytical methods.

A secondary antibody can be rendered detectable by labeling with an enzyme such as horseradish peroxidase (HRP), alkaline phosphatase (AP), β-galactosidase or urease, for example. A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). A secondary antibody can be linked to an enzyme by methods well known in the art (Harlow and Lane, supra, 1988) or can be obtained from a number of commercial sources. For example, goat F(ab')2 anti-human IgG-alkaline phosphatase is a useful detectable secondary antibody that can be purchased from Jackson Immuno-Research (West Grove, Pa.).

A secondary antibody also can be rendered detectable by labeling with a fluorochrome. Such a fluorochrome emits light of ultraviolet or visible wavelength after excitation by light or another energy source. DAPI, fluorescein, Hoechst 33258, R-phycocyanin, B-phycoerythrin, R-phycoerythrin, rhodamine, Texas red or lissamine, for example, is a fluorochrome that can be linked to a secondary antibody and used to detect the presence or absence of a complex. A particularly useful fluorochrome is fluorescein or rhodamine. Methods of conjugating and using these and other suitable fluorochromes are described, for example, in Van Vunakis and Langone, *Methods in Enzymology*, Volume 74, Part C (1991), which is incorporated herein by reference. A secondary antibody linked to a fluorochrome also can be obtained from commercial sources. For example, goat F(ab')$_2$ anti-human IgG-FITC is available from Tago Immunologicals (Burlingame, Calif.).

A secondary antibody also can be labeled with a chemiluminescent marker. Such a chemiluminescent secondary antibody is convenient for sensitive, non-radioactive detection of a complex containing an I-2 polypeptide and can be obtained commercially from various sources such as Amersham Lifesciences, Inc. (Arlington Heights, Ill.).

A secondary antibody further can be rendered detectable by labeling with a radioisotope. An iodine-125 labeled secondary antibody is a particularly useful detectable secondary antibody (see, for example, Harlow and Lane, supra, 1988).

A signal from a detectable secondary antibody can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The assays of the present invention can be forward, reverse or simultaneous as described in U.S. Pat. No. 4,376,110, issued Mar. 8, 1983, to David et al., which is incorporated herein by reference. In the forward assay, each reagent is sequentially contacted with an I-2 polypeptide of the invention. If desired, separation of bound from unbound reagent can be performed before the addition of the next reagent. In a reverse assay, all reagents are pre-mixed prior to contacting with I-2 polypeptide. A modified reverse assay is described in U.S. Pat. No. 4,778,751 issued Oct. 18, 1988, to El Shami et al., which is incorporated herein by reference. In a simultaneous assay, all reagents are separately but contemporaneously contacted with an I-2 polypeptide of the invention. A reagent is any component useful in performing the assays of the present invention, for example, the sample, I-2 polypeptide, detectable secondary antibody, washing buffer or other solutions.

Separation steps for the various assay formats described herein, including the removal of unbound secondary antibody from the complex, can be performed by methods known in the art (Harlow and Lane, supra, 1988). For example, washing with a suitable buffer can be followed by filtration, aspiration or magnetic separation. If the I-2 polypeptide or an immunoreactive fragment thereof is immobilized on a particulate support, such as on microparticles, the particulate material can be centrifuged, if desired, followed by removal of wash liquid. If the I-2 polypeptide or an immunoreactive fragment thereof is immobilized on a membrane, filter or well, a vacuum or liquid absorbing apparatus can be applied to the opposite side of the membrane, filter or well to draw the wash liquid away from the complex.

The invention also provides methods of determining susceptibility to IBD in an individual by obtaining a sample from the individual; contacting the sample with an I-2 polypeptide, or immunoreactive fragment thereof, under conditions suitable to form a complex of the I-2 polypeptide, or the immunoreactive fragment thereof, and antibody to the I-2 polypeptide; and detecting the presence or absence of the complex, where the presence of the complex indicates that the individual is susceptible to IBD.

The term "individual," as used herein, means any animal capable of having inflammatory bowel disease, including a human, non-human primate, rabbit, rat or mouse, provided that the animal does not have inflammatory bowel disease as defined by the clinical, endoscopic and histopathologic parameters disclosed herein. A sample to be assayed according to the methods of the invention can be obtained from any such individual.

As used herein, the term "increased susceptibility to IBD" as indicated by the presence of a complex of I-2 polypeptide and antibody to I-2 polypeptide, means a reduced ability to resist IBD-causing factors, as compared with an individual from whom a sample is obtained that does not form a complex when contacted with I-2 polypeptide or immunoreactive fragment thereof. Increased susceptibility to IBD in an individual does not mean the individual will necessarily develop IBD. However, increased susceptibility to IBD in an individual is associated with an increased probability of having IBD in the future.

The term "immunoreactive fragment," as used in reference to an I-2 polypeptide, means a peptide or polypeptide portion of an I-2 polypeptide that has immunoreactivity as defined by the ability of an anti-I-2 antibody-positive sample to form a complex with the I-2 polypeptide. Thus, the term "immunoreactive fragment of an I-2 polypeptide" as used herein, means a peptide or polypeptide that has an amino acid sequence that is substantially the same as a portion of the amino acid sequence provided as SEQ ID NO: 2 and immunoreactivity as defined by the ability to form a complex with an anti-I-2 antibody-positive sample such as an I-2 reactive serum sample from a Crohn's disease patient. In general, an immunoreactive fragment has from about three amino acids to the full-length of an I-2 polypeptide. An immunoreactive fragment of an I-2 polypeptide can have, for example, at least 5, 8, 10, 12, 15, 18, 20 or 25 amino acids. For example, an immunoreactive fragment of an I-2 polypeptide can be from five to fifty amino acids, from eight to fifty amino acids, or from ten to fifty amino acids. More preferably, an immunoreactive fragment has from eight to twenty amino acids or from ten to twenty amino acids. Most preferably, an immunoreactive fragment has from twelve to twenty amino acids or from fifteen to twenty amino acids.

An immunoreactive fragment of an I-2 polypeptide can be identified by the ability to form a complex with an I-2 reactive sample, for example, an I-2 reactive CD patient serum sample. For example, an immunoreactive fragment of an I-2 polypeptide can be identified by its ability to form a complex when contacted with I-2 reactive CD sera. Assays for the formation of a complex between an antigen and anti-I-2 serum sample are disclosed herein. An ELISA assay can be particularly useful in identifying an immunoreactive fragment of an I-2 polypeptide (see Example IIB).

Identification of a microbial sequence associated with IBD implicates microbes in the pathogenesis of IBD and provides a valuable reagent for ameliorating inflammatory bowel disease. Furthermore, as disclosed herein, the I-2 polypeptide can elicit a T cell response, as demonstrated by the proliferation of murine T cells in response to a GST-I-2 fusion polypeptide (SEQ ID NO: 2), indicating that the I-2 polypeptide antigen can contribute to the etiology of inflammatory bowel disease. Based on identification and isolation of the IBD-associated I-2 sequence, there are provided methods of inducing tolerance in a patient with IBD as well as methods of preventing IBD in a healthy individual.

Thus, the present invention provides methods of inducing tolerance in a patient with inflammatory bowel disease by administering an effective dose of I-2 polypeptide, or tolerogenic fragment thereof, to the patient with IBD. The methods of the invention can be particularly useful for treating a patient having Crohn's disease. In a method of the invention for inducing tolerance, the I-2 polypeptide to be administered can have, for example, the amino acid sequence of SEQ ID NO: 2.

As used herein, the term "patient with inflammatory bowel disease" means a patient having Crohn's disease or ulcerative colitis.

As used herein, the term "effective dose" means the amount of an I-2 polypeptide, or a tolerogenic fragment thereof, useful for inducing tolerance in a patient with IBD. For induction of oral tolerance, for example, multiple smaller oral doses can be administered or a large dose can be administered. Such doses can be extrapolated, for example, from the induction of tolerance in animal models (see, for example, Trentham et al., *Science* 261:1727–1730 (1993), which is incorporated herein by reference).

An effective dose of an I-2 polypeptide or a tolerogenic fragment thereof for inducing tolerance can be administered by methods well known in the art. Oral tolerance is well-recognized in the art as a method of treating autoimmune disease (see, for example, Weiner, *Hospital Practice*, pp. 53–58 (Sep. 15, 1995), which is incorporated herein by reference). For example, orally administered autoantigens suppress several experimental autoimmune models in a disease- and antigen-specific fashion; the diseases include experimental autoimmune encephalomyelitis, uveitis, and myasthenia, collagen- and adjuvant-induced arthritis, and diabetes in the NOD mouse (see, for example, Weiner et al., *Ann. Rev. Immunol.* 12:809–837 (1994), which is incorporated herein by reference). Furthermore, clinical trials of oral tolerance have produced positive results in treating multiple sclerosis, rheumatoid arthritis and uveitis. In addition, parenteral administration of an I-2 polypeptide, or a tolerogenic fragment thereof, can be used to induce tolerance. Subcutaneous injection, for example, can be used to deliver an I-2 polypeptide, or a tolerogenic fragment thereof, to an IBD patient, for example, a patient having Crohn's disease (Johnson, *Ann. Neurology*36(suppl.):S115–S117 (1994), which is incorporated herein by reference).

The term "tolerogenic fragment," as used in reference to an I-2 polypeptide of the invention, means a peptide or polypeptide portion of the polypeptide that has tolerogenic activity as defined by its ability either alone, or in combination with another molecule, to produce a decreased immunological response. Thus, a tolerogenic fragment of an I-2 polypeptide is a peptide or polypeptide that has substantially the same amino acid sequence as a portion of SEQ ID NO: 2 and tolerogenic activity as defined by its ability either alone, or in combination with another molecule, to produce a decreased immunological response. A tolerogenic fragment of an I-2 polypeptide can have from about three amino acids to about 90 amino acids. A tolerogenic fragment of an I-2 polypeptide can have, for example, at least 5, 8, 10, 12, 15, 18, 20 or 25 amino acids. For example, a tolerogenic fragment of an I-2 polypeptide can have from five to fifty amino acids, from eight to fifty amino acids, or from ten to fifty amino acids. More preferably, a tolerogenic fragment has from eight to twenty amino acids or from ten to twenty amino acids. Most preferably, a tolerogenic fragment has from twelve to twenty amino acids or from fifteen to twenty amino acids.

A tolerogenic fragment of an I-2 polypeptide can be identified using a variety of assays, including in vitro assays such as T-cell proliferation or cytokine secretion assays and in vivo assays such as the induction of tolerance in murine models of inflammatory bowel disease. T-cell proliferation assays, for example, are well recognized in the art as predictive of tolerogenic activity (see, for example, Miyahara et al., *Immunol.* 86:110–115 (1995) or Lundin et al, *J. Exp. Med.* 178:187–196 (1993), each of which is incorporated herein by reference). A T-cell proliferation assay can be performed by culturing T-cells with irradiated antigen-presenting cells, such as normal spleen cells, in microtiter wells for 3 days with varying concentrations of the fragment of an I-2 polypeptide to be assayed; adding $^3$H-thymidine; and measuring incorporation of $^3$H-thymidine into DNA. In such an assay, a fragment of an I-2 polypeptide can be tested for activity, for example, at concentrations of 20 µg/ml and 40 µg/ml.

A tolerogenic fragment of an I-2 polypeptide can be identified using a T-cell cytokine secretion assay known in the art. For example, T cells can be cultured with irradiated antigen-presenting cells in microtiter wells with varying concentrations of the fragment of interest and, after three days, the culture supernatants can be assayed for IL-2, IL-4 or IFN-γ as described in Czerinsky et al., *Immunol. Rev.* 119:5–22 (1991), which is incorporated herein by reference.

Primary T-cells for use in a T-cell proliferation assay or cytokine secretion assay, for example, can be isolated from lamina propria or peripheral blood. In addition, a convenient source of T-cells for use in an in vitro assay for tolerogenic activity can be a T-cell line established from an IBD patient such as a Crohn's disease patient, from a murine model of IBD or from a healthy animal immunized with an I-2 polypeptide of the invention. A preferred source of T-cells for use in identifying a tolerogenic fragment of an I-2 polypeptide is a Crohn's disease patient.

A T-cell line can be established from a patient with CD or UC, for example, by culturing T lymphocytes with about 1 µg/ml recombinant I-2 polypeptide or GST-I-2, in the presence of low concentrations of growth-supporting IL-2 (about 10 µg/ml). A T-cell line can be established by culturing T lymphocytes with antigen-presenting cells and feeding the cells on an alternating four to five day cycle with either IL-2 and I-2 polypeptide or IL-2 alone as described in Nanda et al., *J. Exp. Med.* 176:297–302 (1992), which is incorporated herein by reference. A cell line that develops into a reliably proliferating cell line dependent on the presence of I-2 polypeptide is particularly useful in identifying tolerogenic fragments of I-2. The establishment of T-cell lines from small intestinal mucosa is described, for example, in Lundin et al., supra, 1993. T cell lines dependent upon the presence of an I-2 polypeptide and useful for identifying I-2 tolerogenic fragments can be prepared similarly.

A tolerogenic fragment of an I-2 polypeptide also can be identified by its ability to induce tolerance in vivo, as indicated by a decreased immunological response, which can be a decreased T-cell response, such as a decreased proliferative response or cytokine secretion response as described above, or a decreased antibody titer to the antigen. A neonatal or adult mouse can be tolerized with a fragment of an I-2 polypeptide, for example, and a T-cell response or anti-I-2 polypeptide antibody titer can be assayed after challenging by immunization. For example, a neonatal mouse can be tolerized within 48 hours of birth by intraperitoneal administration of about 100 µg of a fragment of an I-2 polypeptide emulsified with incomplete Freund's adjuvant and subsequently immunized with I-2 polypeptide at about 8 weeks of age (see, for example, Miyahara, supra, 1995). An adult mouse can be tolerized intravenously with about 0.33 mg of a fragment of an I-2 polypeptide, administered daily for three days (total dose 1 mg), and immunized one week later with an I-2 polypeptide. A decreased T-cell response, such as decreased proliferation or cytokine secretion, which indicates tolerogenic activity, can be measured using T-cells harvested 10 days after immunization. In addition, a decreased anti-I-2 polypeptide antibody titer, which also indicates tolerogenic activity, can be assayed using blood harvested 4–8 weeks after immunization. Methods for assaying a T-cell response or anti-I-2 polypeptide antibody titer are described above and are well known in the art.

A tolerogenic fragment of an I-2 polypeptide also can be identified using a murine model of inflammatory bowel disease. Neonatal or adult mice having IBD-like disease can be tolerized with a fragment of an I-2 polypeptide as described above, and the T-cell response or anti-I-2 polypeptide antibody titer assayed. A decreased T-cell response or decreased antibody titer to the antigen indicates a decreased immunological response and, thus, serves to identify a tolerogenic fragment of an I-2 polypeptide. In addition, a tolerogenic fragment of an I-2 polypeptide can be identified by the ability to reduce the frequency, time of onset or severity of colitis in a murine model of IBD.

Several well-accepted murine models of inflammatory bowel disease can be useful in identifying a tolerogenic fragment of an I-2 polypeptide of the invention. For example, mice with target disruption of the genes encoding the alpha subunit of the G-protein Gi2, are a well known model exhibiting features of human bowel disease (Hornquist et al., *J. Immunol.* 158:1068–1077 (1997); Rudolph et al., *Nat. Genet.* 10:143–150 (1995), each of which is incorporated herein by reference). Mice deficient in IL-10 as described in Kühn et al., *Cell* 75:263–274 (1993), which is incorporated herein by reference, and mice deficient in IL-2 as described in Sadlack et al., *Cell* 75:253–261 (1993), which is incorporated herein by reference, also have colitis like disease and are useful in identifying a tolerogenic fragment of an I-2 polypeptide of the invention. Furthermore, mice with mutations in T cell receptor (TCR) α, TCR β, TCR β×δ, or the class II major histocompatiblility complex (MHC) as described in Mombaerts et al., *Cell* 75:275–282 (1993), which is incorporated herein by reference, develop inflammatory bowel disease and, thus, are useful in identifying a tolerogenic fragment of an I-2 polypeptide. Similarly, a fragment can be assayed for tolerogenic activity in a SCID mouse reconstituted with CD45RB CD4+ T-cells, which is a well-accepted model of inflammatory bowel disease, as described in Powrie et al., *Immunity* 1:553–562 (1994), which is incorporated herein by reference. Additional animal models of IBD also are well known in the art (see, for example, Podolsky, *Acta Gastroenterol. Belg.* 60:163–165 (1997); and Bregenholt et al., *APMIS* 105: 655–662 (1997), each of which is incorporated herein by reference). Thus, a tolerogenic fragment of an I-2 polypeptide can be readily identified by an in vitro or in vivo assay disclosed herein or by another assay well known in the art.

An immunoreactive or tolerogenic fragment of an I-2 polypeptide can be identified by screening a large collection, or library, of peptides of interest or random peptides for immunoreactivity or tolerogenic activity. For example, a panel of peptides spanning the entire sequence of an I-2 polypeptide can be screened for immunoreactivity or tolerogenic activity as described above. Such a panel can be a panel of 15-mer peptides spanning the sequence of the I-2 polypeptide (SEQ ID NO: 2), each overlapping by three or five residue shifts using the Mimotope cleavable pin technology (Cambridge Research Biochemicals, Wilmington, Del.), as described by Geysen et al., *Science* 235:1184 (1987), which is incorporated herein by reference. The panel is subsequently screened for immunoreactivity or tolerogenic activity using one of the assays described above (see, for example, Miyahara et al., supra, 1995, which is incorporated herein by reference). A library of peptides to be screened also can be a population of peptides related in amino acid sequence to SEQ ID NO: 2 but having one or more amino acids that differ from SEQ ID NO: 2.

Additional peptides to be screened include, for example, tagged chemical libraries of peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid which encodes it. Methods for production of phage display libraries, including vectors and methods of diversifying the population of peptides which are expressed, are well known in the art (see, for example, Smith and Scott, *Methods Enzymol.* 217:228–257 (1993); Scott and Smith, *Science* 249:386–390 (1990); and Huse, WO 91/07141 and WO 91/07149, each of which is incorporated herein by reference). These or other well known methods can be used to produce a phage display library which can be screened, for example, with one of the disclosed assays for immunoreactivity or tolerogenic activity. If desired, a population of peptides can be assayed for activity en masse. For example, to identify an immunoreactive fragment of an I-2 polypeptide, a population of peptides can be assayed for the ability to form a complex with a sample containing anti-I-2 polypeptide reactivity; the active population can be subdivided and the assay repeated in order to isolate the immunoreactive fragment from the population.

An immunoreactive or tolerogenic fragment of an I-2 polypeptide also can be identified by screening, for example, fragments of the polypeptide produced by chemical or proteolytic cleavage. Methods for chemical and proteolytic cleavage and for purification of the resultant protein fragments are well known in the art (see, for example, Deutscher, *Methods in Enzymology*, Vol. 182, "Guide to Protein Purification," San Diego: Academic Press, Inc. (1990), which is incorporated herein by reference). For example, a chemical such as cyanogen bromide or a protease such as trypsin, chymotrypsin, V8 protease, endoproteinase Lys-C, endoproteinase Arg-C or endoproteinase Asp-N can be used to produce convenient fragments of an I-2 polypeptide that can be screened for immunoreactivity or tolerogenic activity using one of the assays disclosed herein.

As used herein, the term "fragment" means a peptide, polypeptide or compound containing naturally occurring amino acids, non-naturally occurring amino acids or chemically modified amino acids. An immunoreactive or tolerogenic fragment of an I-2 polypeptide also can be a peptide mimetic, which is a non-amino acid chemical structure that mimics the structure of a peptide having an amino acid sequence, provided that the peptidomimetic retains immunoreactivity or tolerogenic activity, as defined herein. Such a mimetic generally is characterized as exhibiting similar physical characteristics such as size, charge or hydrophobicity in the same spatial arrangement found in its peptide counterpart. A specific example of a peptide mimetic is a compound in which the amide bond between one or more of the amino acids is replaced, for example, by a carbon-carbon bond or other bond well known in the art (see, for example, Sawyer, *Peptide Based Drug Design*, ACS, Washington (1995), which is incorporated herein by reference).

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains immunoreactivity or tolerogenic activity. Examples of amino acids and amino acids analogs are listed in Gross and Meienhofer, *The Peptides: Analysis, Synthesis, Biology*, Academic Press, Inc., New York (1983), which is incorporated herein by reference. An amino acid also can be an amino acid mimetic, which is a structure that exhibits substantially the same spatial arrangement of functional groups as an amino acid but does not necessarily have both the α-amino and α-carboxyl groups characteristic of an amino acid.

An immunoreactive or tolerogenic fragment of an I-2 polypeptide can be produced or synthesized using methods well known in the art. Such methods include recombinant DNA methods and chemical synthesis methods for production of a peptide. Recombinant methods of producing a peptide through expression of a nucleic acid sequence encoding the peptide in a suitable host cell are well known in the art and are described, for example, in Sambrook et al., *Molecular Cloning: A Laboratory Manual*, 2nd Ed, Vols 1 to 3, Cold Spring Harbor Laboratory Press, New York (1989), which is incorporated herein by reference. The sequence of a nucleic acid molecule encoding an I-2 polypeptide is disclosed herein as SEQ ID NO: 1.

An immunoreactive or tolerogenic fragment of an I-2 polypeptide also can be produced by chemical synthesis, for example, by the solid phase peptide synthesis method of Merrifield et al., *J. Am. Chem. Soc.* 85:2149 (1964), which is incorporated herein by reference. Standard solution methods well known in the art also can be used to synthesize an immunoreactive or tolerogenic fragment useful in the invention (see, for example, Bodanszky, *Principles of Peptide Synthesis*, Springer-Verlag, Berlin (1984) and Bodanszky, *Peptide Chemistry*, Springer-Verlag, Berlin (1993), each of which is incorporated herein by reference). A newly synthesized peptide can be purified, for example, by high performance liquid chromatography (HPLC), and can be characterized using, for example, mass spectrometry or amino acid sequence analysis.

The present invention also provides tolerogenic compositions that contain an I-2 polypeptide and are useful in inducing tolerance in a patient with IBD. In particular, the invention provides compositions including an I-2 polypeptide having substantially the same amino acid sequence as SEQ ID NO: 2, or tolerogenic fragment thereof, combined with a tolerogizing molecule.

In a composition of the invention, the I-2 polypeptide can have, for example, the amino acid sequence SEQ ID NO: 2. A tolerogenic fragment useful in a composition of the invention can have, for example, at least ten contiguous amino acids of SEQ ID NO: 2.

Various molecules are known in the art to cause, promote or enhance tolerance. See, for example, U.S. Pat. No. 5,268,454, and citations therein, which are incorporated herein by reference. As used herein, the term "tolerogizing molecule" means a molecule, compound or polymer that causes, promotes or enhances tolerogenic activity when combined with an I-2 polypeptide of the invention, or fragment thereof. A tolerogizing molecule can be, for example, conjugated to an I-2 polypeptide. Such tolerogizing molecules include, for example, polyethylene glycol and are well known in the art (see, for example, U.S. Pat. No. 5,268,454, supra).

The invention also provides methods of preventing IBD in an individual by administering an effective dose of an I-2 polypeptide, or tolerogenic fragment thereof, to the individual. The methods of the invention are particularly useful for preventing IBD, for example, Crohn's disease in an individual having increased susceptibility to IBD. Such methods can be particularly useful for preventing IBD when an effective dose of the antigen or tolerogenic fragment is administered to a newborn individual.

Enteric bacteria have been shown to play a role in the pathogenesis of several diseases. For example, *H. pylori* has been implicated in pathogenesis of peptic ulcer disease, and antibiotics against *H. pylori* can be used to effectively treat this disease (see, for example, Sontag, *Am. J. Gastroenterol.* 92:1255–1261 (1997); and Pipkin et al., *Helicobactor.* 2:159–171 (1997), each of which is incorporated herein by reference). In Crohn's disease, intestinal inflammation is notable for its frequent responsiveness to antibiotics and susceptibility to bacterial fecal flow (Gui et al., *J. Antimicrob. Chemother.* 39:393–400 (1997); Prantera et al., *Am. J. Gastroenterol.* 91:328–332 (1996); and Janowitz et al., *Inflamm. Bowel. Dis.* 4:29–39 (1998), each of which is incorporated herein by reference). Common intestinal colonists and novel pathogens have been implicated in CD by direct detection or by disease-associated anti-microbial immune responses (Blaser et al., *Gastroenterology* 87:888–894 (1984); Elsaghier et al., *Clin. Exp. Immunol.*

90:503–508 (1992); Del Prete et al., *J. Microbiol. Methods* 33:105–114 (1998); Metcalf, *British Medical Journal* 316:166 (1998), each of which is incorporated herein by reference; and Sendid et al., supra, 1996). Furthermore, in most animal models of chronic colitis, lumenal microorganisms are a necessary co-factor for disease. Dietary antigens also have been implicated in IBD pathogenesis (Sonnenberg, *Gut* 31:1037–1040 (1990); Davidson et al., *Clin. Exp. Immunol.* 35:147–148 (1979); and Knoflach et al., *Gastroenterology* 92:479–485 (1987), each of which is incorporated herein by reference). Despite extensive research, the pathogenic organism remains to be identified.

As disclosed herein, colonic microbes harbored in inflamed lesions in Crohn's disease patients contain a nucleic acid sequence encoding the I-2 polypeptide antigen (SEQ ID NO: 2). Based on this finding, the microbial organism can be isolated and used for discovery of agents that reduce the viability or growth of the organism, thereby diminishing the immune stimulus contributing to Crohn's and ameliorating symptoms of the disease.

Thus, the invention provides a method of identifying an agent useful in treating inflammatory bowel disease. The method includes the steps of obtaining a specimen of an enteric microbe from a patient with inflammatory bowel disease; isolating from the specimen a microbial species that includes a nucleic acid molecule encoding an I-2 polypeptide; contacting the microbial species with an agent; and assaying for reduced growth or viability of the microbial species as compared to the growth or viability in the absence of the agent, where the reduced growth or viability of the microbial species indicates that the agent is an agent useful in treating inflammatory bowel disease. The methods of the invention can be particularly useful for screening agents which are antibiotics and for identifying agents for the treatment of Crohn's disease. One skilled in the art understands that the microbial species which is contacted with an agent in the methods of the invention can be a single microbial species or can be a mixture of two or more microbial species, where at least one species contains a nucleic acid sequence encoding an I-2 polypeptide.

Isolation of a microbial species that includes a nucleic acid molecule encoding an I-2 polypeptide can be performed by culturing the I-2 positive specimen on a variety of mediums and under aerobic and anaerobic conditions as described in Example IV; isolates are subsequently screened for the presence of the I-2 sequence using, for example, PCR analysis. Exemplary culture conditions are set forth in FIG. 7.

As used herein, the term "agent" means a biological or chemical compound such as a simple or complex organic molecule, a peptide, a protein, an antibody, a lipid or an oligonucleotide.

An agent identified by the methods of the invention reduces the viability or growth of a microbial species that contains a nucleic acid molecule encoding an I-2 polypeptide. Thus, an agent useful in treating IBD can be an agent that functions to kill or slow the growth of a microbial species that contains a nucleic acid molecule encoding an I-2 polypeptide. An agent useful in treating IBD can be a bacteriostatic or bacteriocidal agent such as a bacterial antibiotic, which is a molecule that is produced by a microorganism or a plant, or a chemical derivative of such a molecule, that can reduce the growth or viability of a bacterial species that contains a nucleic acid molecule encoding an I-2 polypeptide. One skilled in the art understands that an agent useful in treating IBD can function by a variety of mechanisms, for example, by inhibiting microbial protein synthesis, inhibiting microbial DNA synthesis, inhibiting microbial cell wall synthesis or inhibiting synthesis of an essential nutrient of a microbial species that contains a nucleic acid molecule encoding an I-2 polypeptide. Such an agent can selectively reduce the viability or growth of a particular microbial species that contains a nucleic acid molecule encoding an I-2 polypeptide. An agent useful in treating IBD also can have activity in reducing the growth or viability of a broad spectrum of microbes. One skilled in the art understands that, preferably, an agent useful in treating IBD reduces the growth or viability of a microbial species that contains a nucleic acid molecule encoding an I-2 polypeptide without significantly altering the growth or viability of mammalian cells, especially human cells.

As used herein, the term "agent useful in treating IBD" means an agent that reduces the severity, frequency, or time of onset of one or more symptoms of inflammatory bowel disease.

Although animal models of inflammatory bowel disease are known, these models do not involve an antigen associated with human IBD. Based on the disclosed isolation of the IBD-associated I-2 polypeptide antigen (SEQ ID NO: 2) and the demonstration that murine T cells are responsive to this antigen (see Example III), the invention provides novel animal models for IBD, in which disease is initiated with the I-2 antigen associated with human disease. Thus, superior IBD animal models are provided for identifying new IBD therapeutics, including antibiotics, anti-inflammatories and other drugs.

In particular, the invention provides a method of identifying an agent useful in treating inflammatory bowel disease by administering an I-2 polypeptide to a non-human animal, whereby one or symptoms of IBD are exhibited; administering an agent to the non-human animal; and assaying the level of the one or more symptoms characteristic of IBD, where a reduction in the level of the one or more symptoms as compared to a control level indicates that the agent is an agent useful in treating IBD. The methods of the invention can be applied, for example, to identification of agents useful in treating Crohn's disease. The I-2 polypeptide administered can have, for example, the amino acid sequence SEQ ID NO: 2. A non-human animal particularly useful in the methods of the invention can be, for example, a mouse deficient in Gαi2, TCRα or IL-10.

As set forth above, the term "agent" means a biological or chemical compound such as a simple or complex organic molecule, a peptide, a protein, an antibody, a lipid or an oligonucleotide. An agent can be, for example, an antibiotic or anti-inflammatory compound.

The methods of the invention rely on the use of a non-human animal, which can exhibit one or more symptoms of inflammatory bowel disease in response to an antigenic trigger. Any non-human animal model of disease can be useful in the methods of the invention including non-human primate, rat or mouse model of IBD. A variety of mouse models of IBD well known in the art can be particularly useful in the invention (see, for example, Podolsky, supra, 1997; Bregenholt et al., supra, 1997). Such mouse models include those described hereinabove, for example, mice deficient in Gαi2 (Gαi2 -/-; Rudolph et al., supra, 1995); mice deficient in IL-10 (IL-10 -/-; Kühn et al., supra, 1993); mice deficient in TCRα (TCRα -/-); mice deficient in TCRβ (TCRβ -/-); mice deficient in keratin 8; mice deficient in IL-2 (IL-2 -/-; Sadlack, supra, 1993); and SCID mice reconstituted with CD45RB CD4+ T cells (Powrie et al., supra, 1994). Non-human animal models useful in the methods of the invention also include animals expressing transgenes for human HLA-B27 (with β2-microglobulin) or animals expressing a dominant negative construct that functionally blocks N-cadherin (Podolsky, supra, 1997).

One skilled in the art understands that, in order to initiate one or more symptoms of IBD in a non-human animal model, an I-2 polypeptide of the invention can be administered by a variety of routes. Preferred administration of an I-2 polypeptide to initiate one or more symptoms of IBD in a non-human animal model of the disease is by enema administration or by administering a cellular composition in which the I-2 polypeptide is expressed using *E. coli.*

Local administration of free antigen can be achieved by enema, for example, as described in Mahler et al., *Am. J. Physiol.* 274: G544-G551 (1998). An I-2 polypeptide also can be administered by colonization of the mouse colon with antigen-bearing microorganisms, for example, *E. coli* (Cahill et al., *Infect Immuno.*, 65:3126–3131 (1997)) or another bacterial species (Kullberg et al., *Infect. Immun.* 66:5157–5166 (1998); Li et al., *Infect. Immun.* 66:5477–5484 (1998); and Cahill, supra, 1997). In a non-human animal model of IBD, one or more symptoms of IBD also can be induced using a T cell line reactive with a bacterial antigen, where the T cell line is derived from a colitis susceptible mouse strain. Such a T cell line can be, for example, an E. coli reactive T cell line produced from C3H/HeJBir mice (Cong et al., *J. Exp. Med.* 187:855–864 (1998)). A C.B-17Scid mouse also can be colonized with antigen-bearing bacteria, either naturally or by intra-intestinal infection (Kullberg et al., supra, 1998; Li et al., supra, 1998; and Cong et al., supra, 1998). Transfer of a T cell line into such a mouse results in a robust antigen-specific inflammatory bowel disease model (Kullberg et al., supra, 1998; and Cong et al., supra, 1998).

The following examples are intended to illustrate but not limit the present invention.

EXAMPLE I

Identification of the I-2 and I-1 Target Antigens

This example describes isolation of novel microbial nucleic acid sequences encoding the I-1 and I-2 polypeptides.

A. Representational difference analysis

Representational difference analysis (RDA), which uses PCR driven subtractive cloning to identify DNA sequences found preferentially in an infected area, was utilized to examine sequences differentially present in involved versus uninvolved CD mucosa.

RDA was performed essentially as described in Chang et al., *Science* 266:1865–1869 (1994), which is incorporated herein by reference. Briefly, mononuclear cells from the lamina propria of a Crohn's disease patient were isolated from an area with ulcerations (tester cells) and from an area macroscopically free of disease (driver cells), and DNA purified from each cell population. Using RDA, the DNA sequences from the area free of disease (driver DNA) were subtracted from the DNA found at the site of ulceration (tester DNA), leaving sequences preferentially found in the inflamed area.

Four sequences were obtained, two of which were human sequences. The remaining two sequences, designated I-1 and I-2, showed no significant homology to any human genes. The I-2 nucleic acid sequence (SEQ ID NO: 1) and encoded polypeptide (SEQ ID NO: 2) are shown in FIG. 1A. The I-1 nucleic acid sequence (SEQ ID NO: 3) and two encoded open reading frames (SEQ ID NOS: 4 and 5) are shown in FIG. 1B.

B. PCR analysis of archived paraffin embedded tissue samples

Paraffin embedded tissue samples from CD patients, UC patients, or non-IBD controls were subject to PCR analysis. Briefly, sample was amplified with the I-2 specific primers 5'-CCGTGGGCATCCAGTCCG-3' (SEQ ID NO: 9) and 5'-TCTGCTCATACACGTCACG-3' (SEQ ID NO: 10) using standard PCR conditions with a final concentration of 4 mM $MgCl_2$. In particular, the reactions consisted of 26.75 µl $H_2O$; 5.0 µl 10× PCR Buffer; 5.0 µl 25 mM $MgCl_2$; 1.0 µl 10 mM each dNTP; 1.0 µl each of SEQ ID NOS: 9 and 10; and 0.25 µp Taq polymerase (5 units/µl). The reactions were incubated at 94° C. for 5 minutes; followed by 39 cycles of 94° C. for 30 seconds/65° C. for 30 seconds and 72° C. for 30 seconds, followed by a final 5 minute extension at 72° C. Reactions were analyzed on 2% agarose, with the presence of the I-2 sequence indicated by the expected 285 bp fragment.

As shown in FIG. 3, the I-2 sequence (SEQ ID NO: 1) was present significantly more frequently in involved CD samples than in UC samples or non-IBD samples. These results indicate that the I-2 polypeptide antigen (SEQ ID NO: 2) is associated with inflammatory bowel disease, in particular, with Crohn's disease.

EXAMPLE II

Differential Reactivity of IBD Patient and Normal Sera to the I-2 Polypeptide

This example demonstrates that the I-2 polypeptide is differentially reactive with Crohn's disease patient sera as compared to normal sera.

A. GST-I-2 fusion protein

The full-length I-2 encoding nucleic acid sequence (SEQ ID NO: 1) was cloned into the GST expression vector pGEX. After expression in *E. coli*, the protein was purified on a GST column. The purified protein was shown to be of the expected molecular weight by silver staining, and had anti-GST reactivity upon western analysis.

B. ELISA analysis

ELISA analysis was performed with GST-I-2 (SEQ ID NO: 2) fusion polypeptide using diluted patient or normal serum. Reactivity was determined after subtracting reactivity to GST alone. Varying dilutions of CD sera and sera from normal individuals were assayed for IgG reactivity to the GST-I-2 fusion polypeptide. As shown in FIG. 4A, dilutions of 1:100 to 1:1000 resulted in significantly higher anti-L-2 polypeptide reactivity for the CD sera as compared to normal sera. These results indicate that the I-2 polypeptide (SEQ ID NO: 2) is differentially reactive with Crohn's disease sera as compared to normal sera.

Serum IgA reactivity of UC, CD and normal sera to the I-2 polypeptide (SEQ ID NO: 2) was assayed as described below. As shown in FIG. 4B, using a cutoff that is two standard deviations above the mean value for the normal population, nine of ten CD values were positive, while none of the normal serum samples were positive. Furthermore, seven of ten Crohn's disease patients showed an $OD_{405}$ greater than 0.3, while none of the UC or normal samples were positive by this measure. These results indicate that immunoreactivity to the I-2 polypeptide, in particular, IgA immunoreactivity, can be used to diagnose Crohn's disease.

Human IgA and IgG antibodies that bind the I-2 polypeptide (SEQ ID NO: 2) were detected by direct ELISA assays essentially as follows. Plates (Immulon 3; DYNEX Technologies; Chantilly, Va.) were coated overnight at 4° C. with 100 µl/well GST-I-2 fusion polypeptide (5 µg/ml in borate buffered saline, pH 8.5). After three washes in 0.05% Tween 20 in phosphate buffered saline (PBS), the plates were blocked with 150 µl/well of 0.5% bovine serum albumin in PBS, pH 7.4 (BSA-PBS) for 30 minutes at room temperature. The blocking solution was then replaced with 100 µl/well of Crohn's disease serum, ulcerative colitis serum, or normal control serum, diluted 1:100. The plates were then incubated for 2 hours at room temperature and washed as before. Alkaline phosphatase conjugated secondary antibody [goat anti-human IgA (α-chain specific), Jackson ImmunoResearch, West Grove, Pa.] was added to the IgA plates at a dilution of 1:1000 in BSA-PBS. For IgG reactivity, alkaline phosphatase conjugated secondary antibody (goat anti-human IgG (γ-chain specific), Jackson ImmunoResearch) was added. The plates were incubated for 2 hours at room temperature before washing three times with 0.05% Tween 20/PBS followed by another three washes with Tris buffered normal saline, pH 7.5. Substrate solution (1.5 mg/ml disodium P-nitrophenol phosphate (Aresco; Solon, Ohio.) in 2.5 mM $MgCl_2$, 0.01 M Tris, pH 8.6) was added at 100 µl/well, and color allowed to develop for one hour. The plates were then analyzed at 405 nm.

C. Histological analysis

Rabbit anti-I-2 antibodies are prepared using purified GST-I-2 fusion protein as the immunogen. GST binding antibodies are removed by adherence to GST bound to an agarose support (Pierce), and the rabbit sera validated for anti-I-2 immunoreactivity by ELISA analysis.

Slides are prepared from paraffin embedded biopsy specimens from CD, UC and normal controls. Hematoxylin and eosin staining are performed, followed by incubation with I-2 specific antiserum. Binding of antibodies is detected with peroxidase labeled anti-rabbit secondary antibodies (Pierce). The assay is optimized to maximize the signal to background and the distinction between CD and control populations.

EXAMPLE III

Reactivity of CD4+ T Cells with the I-2 Polypeptide

This example demonstrates that T cells derived from normal mice proliferate in response to the I-2 antigen (SEQ ID NO: 2).

CD4+ T cells were isolated from normal C57BL/6J mice, and T cell proliferation assayed in response to the I-2 antigen as follows. To prepare the CD4+ T cells, spleens from 8–10 week old female mice were removed and placed into cell suspension. The cells were depleted for B cells and antigen presenting cells (APCs) using nylon wool and then depleted for CD8+ T cells using anti-CD8 magnetic beads. Flow cytometry was used to determine the purity of the CD4+ T cell suspension.

For preparing APCs, spleens from 8–10 week old females are removed, placed into cell suspension, and pulsed overnight with 0, 2, 10, or 15 µg/ml of the I-2 polypeptide. The APCs are irradiated with 3,000 rads before being added to the T cell cultures. To assay for antigen specific proliferation of T cells, $4 \times 10^5$ CD4+ T cells/well were incubated with $4 \times 10^5$ antigen-pulsed APCs/well in a 96-well flat bottomed tissue culture plate at 37 C in 5% $CO_2$ humidified air. After varying periods of incubation, 0.5 µCi of [$^3$H]-thymidine was added to each culture for the last 18 hours of incubation. The cells were harvested and proliferation assessed as the amount of [$^3$H]-thymidine into cell DNA by scintillation counting.

As shown in FIG. 5, the I-2 polypeptide antigen (SEQ ID NO: 2) stimulates T cell proliferation at concentrations of 5 µg/ml and 25 µg/ml. These results demonstrate that the I-2 polypeptide (SEQ ID NO: 2) associated with human inflammatory bowel disease can elicit a T cell response by murine cells and indicate that an I-2 polypeptide can contribute to the etiology of inflammatory bowel disease.

B. Cytokine expression in response to the I-2 polypeptide

A role for regulatory T cells is supported by studies with CD45

-continued

```
tat gag cag atc t                                                     302
Tyr Glu Gln Ile
            100

<210> SEQ ID NO 2
<211> LENGTH: 100
<212> TYPE: PRT
<213> ORGANISM: Unknown
<220> FEATURE:
<223> OTHER INFORMATION: Microbial organism from the human gut

<400> SEQUENCE: 2

Asp Leu Ala Ser Ala Val Gly Ile Gln Ser Gly Ser Ile Phe His His
 1               5                  10                  15

Phe Lys Ser Lys Asp Glu Ile Leu Arg Ala Val Met Glu Glu Thr Ile
            20                  25                  30

His Tyr Asn Thr Ala Met Met Arg Ala Ser Leu Glu Glu Ala Ser Thr
        35                  40                  45

Val Arg Glu Arg Val Leu Ala Leu Ile Arg Cys Glu Leu Gln Ser Ile
    50                  55                  60

Met Gly Gly Ser Gly Glu Ala Met Ala Val Leu Val Tyr Glu Trp Arg
65                  70                  75                  80

Ser Leu Ser Ala Glu Gly Gln Ala His Val Leu Ala Leu Arg Asp Val
                85                  90                  95

Tyr Glu Gln Ile
            100

<210> SEQ ID NO 3
<211> LENGTH: 392
<212> TYPE: DNA
<213> ORGANISM: Unknown
<220> FEATURE:
<223> OTHER INFORMATION: Microbial Organism from the human gut
<221> NAME/KEY: CDS
<222> LOCATION: (2)...(346)
<221> NAME/KEY: misc_feature
<222> LOCATION: (1)...(392)
<223> OTHER INFORMATION: n = A,T,C or G

<400> SEQUENCE: 3 a gat ctt gag cgt cat gag tgc ctg ggg tac gcc ttt tca tcg cgt ccg   49
  Asp Leu Glu Arg His Glu Cys Leu Gly Tyr Ala Phe Ser Ser Arg Pro
   1               5                  10                  15 gcg gat cga gag tgg gtg ttt ttt cag ggc acg gtt tcc tac aag gta    97
Ala Asp Arg Glu Trp Val Phe Phe Gln Gly Thr Val Ser Tyr Lys Val
            20                  25                  30 cga gtg gcc agc cgt ttg ctc atc aat gaa agc cgg gca ttg atg tcg   145
Arg Val Ala Ser Arg Leu Leu Ile Asn Glu Ser Arg Ala Leu Met Ser
        35                  40                  45 gcg gca ttg gat ggt ttt ggc ata gtg ctc ggc ccg caa gac ttc ctg   193
Ala Ala Leu Asp Gly Phe Gly Ile Val Leu Gly Pro Gln Asp Phe Leu
    50                  55                  60 cga acg gcg ttg gcg agt ggc gag ttg gtg cgg gtg ttg ccg gag ttt   241
Arg Thr Ala Leu Ala Ser Gly Glu Leu Val Arg Val Leu Pro Glu Phe
65                  70                  75                  80 gag gct ccg agt cgg tcg atg cat ttg gtc tac acc gca aac cgc cag   289
Glu Ala Pro Ser Arg Ser Met His Leu Val Tyr Thr Ala Asn Arg Gln
                85                  90                  95 cgt acc gcc aag ttg cgc tgc ttt gtc gag act gtg ctg gga cgt ttt   337
Arg Thr Ala Lys Leu Arg Cys Phe Val Glu Thr Val Leu Gly Arg Phe
            100                 105                 110 ggt ccg gta tgaaggagca ccaccgtggc ggtcgccggg angcacctaa            386
Gly Pro Val
```

```
Gly Pro Val
        115 agatct                                                                    392

<210> SEQ ID NO 4
<211> LENGTH: 115
<212> TYPE: PRT
<213> ORGANISM: Unknown
<220> FEATURE:
<223> OTHER INFORMATION: Microbial organism from the human gut

<400> SEQUENCE: 4

Asp Leu Glu Arg His Glu Cys Leu Gly Tyr Ala Phe Ser Ser Arg Pro
 1               5                  10                  15

Ala Asp Arg Glu Trp Val Phe Phe Gln Gly Thr Val Ser Tyr Lys Val
            20                  25                  30

Arg Val Ala Ser Arg Leu Leu Ile Asn Glu Ser Arg Ala Leu Met Ser
        35                  40                  45

Ala Ala Leu Asp Gly Phe Gly Ile Val Leu Gly Pro Gln Asp Phe Leu
    50                  55                  60

Arg Thr Ala Leu Ala Ser Gly Glu Leu Val Arg Val Leu Pro Glu Phe
65                  70                  75                  80

Glu Ala Pro Ser Arg Ser Met His Leu Val Tyr Thr Ala Asn Arg Gln
                85                  90                  95

Arg Thr Ala Lys Leu Arg Cys Phe Val Glu Thr Val Leu Gly Arg Phe
            100                 105                 110

Gly Pro Val
        115

<210> SEQ ID NO 5
<211> LENGTH: 114
<212> TYPE: PRT
<213> ORGANISM: Unknown
<220> FEATURE:
<223> OTHER INFORMATION: Microbial Organism from the human gut
<221> NAME/KEY: VARIANT
<222> LOCATION: (1)...(114)
<223> OTHER INFORMATION: Xaa = Any Amino Acid

<400> SEQUENCE: 5

Arg Thr Arg Arg Ile Ser Leu Pro His Lys Lys Leu Ala Arg Asn Gly
 1               5                  10                  15

Val Leu Tyr Ser His Gly Ala Thr Gln Glu Asp Ile Phe Ala Pro Cys
            20                  25                  30

Gln His Arg Arg Cys Gln Ile Thr Lys Ala Tyr His Glu Ala Arg Leu
        35                  40                  45

Val Glu Gln Ser Arg Arg Gln Arg Thr Ala Leu Gln His Pro His Gln
    50                  55                  60

Arg Leu Lys Leu Ser Arg Thr Pro Arg His Met Gln Asp Val Gly Cys
65                  70                  75                  80

Val Ala Leu Thr Gly Gly Leu Gln Ala Ala Lys Asp Leu Ser His Gln
                85                  90                  95

Ser Thr Lys Thr Arg Tyr Ser Pro Ala Gly Gly His Arg Asp Gly Pro
            100                 105                 110

Xaa Val

<210> SEQ ID NO 6
<211> LENGTH: 190
<212> TYPE: PRT
```

-continued

<213> ORGANISM: Clostridium pasteurianum

<400> SEQUENCE: 6

```
Met Asn Lys Thr Lys Asp Asn Ile Phe Tyr Ser Ala Ile Lys Val Phe
 1               5                  10                  15

Ser Asn Asn Gly Tyr Asn Gly Ala Thr Met Asp Glu Ile Ala Ser Asn
            20                  25                  30

Ala Gly Val Ala Lys Gly Thr Leu Tyr Tyr His Phe Lys Ser Lys Glu
        35                  40                  45

Glu Ile Phe Lys Tyr Ile Ile Glu Glu Gly Val Asn Leu Met Lys Asn
    50                  55                  60

Glu Ile Asp Glu Ala Thr Asp Lys Glu Lys Thr Ala Leu Glu Lys Leu
65                  70                  75                  80

Lys Ala Val Cys Arg Val Gln Leu Asn Leu Ile Tyr Lys Asn Arg Asp
                85                  90                  95

Phe Phe Lys Val Ile Ala Ser Gln Leu Trp Gly Lys Glu Leu Arg Gln
            100                 105                 110

Leu Glu Leu Arg Asp Ile Met Arg Asn Tyr Val Val His Ile Glu Glu
        115                 120                 125

Phe Val Lys Asp Ala Met Glu Ala Gly Ser Ile Lys Lys Gly Asn Ser
    130                 135                 140

Leu Phe Val Ala Tyr Ala Phe Leu Gly Thr Leu Cys Ser Val Ser Leu
145                 150                 155                 160

Tyr Glu Val Ile Asn Ala Glu Asn Asp Asn Ile Asn Asn Thr Ile Glu
                165                 170                 175

Asn Leu Met Asn Tyr Ile Leu Asn Gly Ile Gly Leu Gln Asn
            180                 185                 190
```

<210> SEQ ID NO 7
<211> LENGTH: 200
<212> TYPE: PRT
<213> ORGANISM: Mycobacterium tuberculosis

<400> SEQUENCE: 7

```
Met Asp Arg Val Ala Gly Gln Val Asn Ser Arg Arg Gly Glu Leu Leu
 1               5                  10                  15

Glu Leu Ala Ala Ala Met Phe Ala Glu Arg Gly Leu Arg Ala Thr Thr
            20                  25                  30

Val Arg Asp Ile Ala Asp Gly Ala Gly Ile Leu Ser Gly Ser Leu Tyr
        35                  40                  45

His His Phe Ala Ser Lys Glu Glu Met Val Asp Glu Leu Leu Arg Gly
    50                  55                  60

Phe Leu Asp Trp Leu Phe Ala Arg Tyr Arg Asp Ile Val Asp Ser Thr
65                  70                  75                  80

Ala Asn Pro Leu Glu Arg Leu Gln Gly Leu Phe Met Ala Ser Phe Glu
                85                  90                  95

Ala Ile Glu His His His Ala Gln Val Val Ile Tyr Gln Asp Glu Ala
            100                 105                 110

Gln Arg Leu Ala Ser Gln Pro Arg Phe Ser Tyr Ile Glu Asp Arg Asn
        115                 120                 125

Lys Gln Gln Arg Lys Met Trp Val Asp Val Leu Asn Gln Gly Ile Glu
    130                 135                 140

Glu Gly Tyr Phe Arg Pro Asp Leu Asp Val Asp Leu Val Tyr Arg Phe
145                 150                 155                 160

Ile Arg Asp Thr Thr Trp Val Ser Val Arg Trp Tyr Arg Pro Gly Gly
```

-continued

```
                    165                 170                 175
Pro Leu Thr Ala Gln Val Gly Gln Gln Tyr Leu Ala Ile Val Leu
            180                 185                 190
Gly Gly Ile Thr Lys Glu Gly Val
        195                 200

<210> SEQ ID NO 8
<211> LENGTH: 192
<212> TYPE: PRT
<213> ORGANISM: Auifex aeolicus

<400> SEQUENCE: 8

Met Tyr Ile Leu Leu Phe Met Gly Glu Lys Arg Ser Asp Thr Lys Glu
  1               5                  10                  15
Lys Ile Leu Ser Ser Ala Leu Lys Leu Phe Ser Lys Lys Gly Phe Lys
             20                  25                  30
Glu Thr Thr Ile Lys Asp Ile Ala Lys Glu Val Gly Ile Thr Glu Gly
         35                  40                  45
Ala Ile Tyr Arg His Phe Thr Ser Lys Glu Glu Ile Ile Lys Ser Leu
     50                  55                  60
Leu Glu Ser Ile Thr Lys Glu Leu Arg His Lys Leu Glu Val Ala Leu
 65                  70                  75                  80
Gln Arg Gly Glu Thr Asp Glu Ile Leu Glu Ser Ile Val Asp Thr
                 85                  90                  95
Leu Ile Asp Tyr Ala Phe Ser Asn Pro Glu Ser Phe Arg Phe Leu Asn
            100                 105                 110
Leu Tyr His Leu Leu Lys Glu Tyr Gly Glu Val Lys Asn Leu Pro Gly
        115                 120                 125
Glu Leu Ile Leu Lys Phe Leu Asn Gly Leu Tyr Leu Lys Arg Lys Leu
    130                 135                 140
Lys Thr Tyr Pro Glu Ile Ala Leu Ala Val Val Thr Gly Ser Val Glu
145                 150                 155                 160
Arg Val Phe Ile Phe Lys Glu Arg Asn Phe Leu Asp Tyr Asp Glu Glu
                165                 170                 175
Thr Ile Lys Lys Glu Leu Lys Lys Val Leu Lys Ser Ala Ile Leu Ala
            180                 185                 190

<210> SEQ ID NO 9
<211> LENGTH: 18
<212> TYPE: DNA
<213> ORGANISM: Unknown
<220> FEATURE:
<223> OTHER INFORMATION: Microbial Organism from the human gut

<400> SEQUENCE: 9
ccgtgggcat ccagtccg                                                 18

<210> SEQ ID NO 10
<211> LENGTH: 19
<212> TYPE: DNA
<213> ORGANISM: Unknown
<220> FEATURE:
<223> OTHER INFORMATION: Microbial Organism from the human gut

<400> SEQUENCE: 10
tctgctcata cacgtcacg                                                19
```

We claim:

1. An isolated nucleic acid molecule, comprising a nucleic acid sequence encoding substantially the same amino acid sequence as SEQ ID NO: 2.

2. The isolated nucleic acid molecule of claim 1, comprising the nucleic acid sequence SEQ ID NO: 1.

* * * * *